United States Patent
Romano et al.

(10) Patent No.: US 10,031,588 B2
(45) Date of Patent: *Jul. 24, 2018

(54) DEPTH MAPPING WITH A HEAD MOUNTED DISPLAY USING STEREO CAMERAS AND STRUCTURED LIGHT

(71) Applicant: Facebook, Inc., Menlo Park, CA (US)

(72) Inventors: Nitay Romano, Geva Binyamin (IL); Nadav Grossinger, Foster City, CA (US); Yair Alpern, Kfar Saba (IL); Emil Alon, Pardes Hana (IL); Guy Raz, Binyamina (IL)

(73) Assignee: Facebook, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/827,816

(22) Filed: Nov. 30, 2017

(65) Prior Publication Data
US 2018/0157342 A1    Jun. 7, 2018

Related U.S. Application Data

(63) Continuation of application No. 15/077,540, filed on Mar. 22, 2016, now Pat. No. 9,870,068.
(Continued)

(51) Int. Cl.
G06F 3/03    (2006.01)
H04N 13/04    (2006.01)
(Continued)

(52) U.S. Cl.
CPC ......... G06F 3/0317 (2013.01); H04N 13/025 (2013.01); H04N 13/0253 (2013.01);
(Continued)

(58) Field of Classification Search
CPC ............... G06F 3/0317; H04N 13/025; H04N 13/0253; H04N 13/044; H04N 2013/0081; H01S 5/0085; H01S 5/423
(Continued)

(56) References Cited

U.S. PATENT DOCUMENTS 5,335,288 A    8/1994 Faulkner
5,638,220 A    6/1997 Ohtomo et al.
(Continued)

FOREIGN PATENT DOCUMENTS

CN    1414420 A    4/2003
CN    101451826 A    6/2009
(Continued)

OTHER PUBLICATIONS

Canadian Intellectual Property Office, Office Action, Canadian Patent Application No. 2,924,622, dated Feb. 6, 2017, three pages.
(Continued)

*Primary Examiner* — Stephen G Sherman
(74) *Attorney, Agent, or Firm* — Fenwick & West LLP

(57) ABSTRACT

A tracking system generates a structured light pattern in a local area. The system includes an array of lasers that generate light. The array of lasers includes a plurality of lasers and an optical element. The plurality of lasers are grouped into at least two subsets of lasers, and each of the at least two subsets of lasers is independently switchable. The optical element includes a plurality of cells that are each aligned with a respective subset of the array of lasers. Each cell receives light from a corresponding laser of the array of lasers, and each cell individually applies a modulation to the received light passing through the cell to form a corresponding portion of the structured light pattern that is projected onto a local area.

20 Claims, 14 Drawing Sheets

Related U.S. Application Data

(60) Provisional application No. 62/136,549, filed on Mar. 22, 2015.

(51) Int. Cl.

| | | |
|---|---|---|
| *H04N 13/02* | (2006.01) | |
| *H04N 13/25* | (2018.01) | |
| *H04N 13/254* | (2018.01) | |
| *H04N 13/344* | (2018.01) | |
| *H04N 13/00* | (2018.01) | |
| *H01S 5/42* | (2006.01) | |
| *H01S 5/00* | (2006.01) | |

(52) U.S. Cl.
CPC ........... *H04N 13/044* (2013.01); *H04N 13/25* (2018.05); *H04N 13/254* (2018.05); *H04N 13/344* (2018.05); *H01S 5/0085* (2013.01); *H01S 5/423* (2013.01); *H04N 2013/0081* (2013.01)

(58) Field of Classification Search
USPC .......................................................... 345/158
See application file for complete search history.

(56) References Cited

U.S. PATENT DOCUMENTS

| | | | |
|---|---|---|---|
| 6,040,910 | A | 3/2000 | Wu et al. |
| 6,102,552 | A | 8/2000 | Tullis |
| 6,549,288 | B1 | 4/2003 | Migdal et al. |
| 6,714,234 | B1 | 3/2004 | Hillis |
| 7,176,440 | B2 | 2/2007 | Cofer et al. |
| 7,440,590 | B1 | 10/2008 | Hassebrook et al. |
| 8,766,952 | B2 | 7/2014 | Lee et al. |
| 9,870,068 | B2 * | 1/2018 | Romano .............. H04N 13/025 |
| 2002/0125435 | A1 | 9/2002 | Cofer et al. |
| 2002/0181742 | A1 | 12/2002 | Wallace et al. |
| 2003/0218761 | A1 | 11/2003 | Tomasi et al. |
| 2004/0004723 | A1 | 1/2004 | Seko et al. |
| 2004/0108990 | A1 | 6/2004 | Lieberman et al. |
| 2004/0119833 | A1 | 6/2004 | Duncan |
| 2005/0057741 | A1 | 3/2005 | Anderson |
| 2006/0176468 | A1 | 8/2006 | Anderson et al. |
| 2007/0120834 | A1 | 5/2007 | Boillot |
| 2008/0062123 | A1 | 3/2008 | Bell |
| 2008/0088588 | A1 | 4/2008 | Kitaura |
| 2008/0106746 | A1 | 5/2008 | Shpunt et al. |
| 2008/0256494 | A1 | 10/2008 | Greenfield |
| 2008/0317332 | A1 | 12/2008 | Ivanov et al. |
| 2009/0002342 | A1 | 1/2009 | Terada et al. |
| 2009/0016572 | A1 | 1/2009 | Hassebrook et al. |
| 2009/0027337 | A1 | 1/2009 | Hildreth |
| 2009/0167682 | A1 | 7/2009 | Yamashita et al. |
| 2009/0189858 | A1 | 7/2009 | Lev et al. |
| 2009/0195659 | A1 | 8/2009 | Nagata et al. |
| 2009/0322673 | A1 | 12/2009 | Cherradi El Fadili |
| 2010/0189372 | A1 | 7/2010 | Chen et al. |
| 2011/0007037 | A1 | 1/2011 | Ogawa |
| 2011/0019056 | A1 | 1/2011 | Hirsch et al. |
| 2011/0158508 | A1 | 6/2011 | Shpunt et al. |
| 2011/0254810 | A1 | 10/2011 | Lee et al. |
| 2012/0051588 | A1 | 3/2012 | McEldowney |
| 2012/0162140 | A1 | 6/2012 | Lee et al. |
| 2012/0194561 | A1 | 8/2012 | Grossinger et al. |
| 2012/0200829 | A1 | 8/2012 | Bronstein et al. |
| 2013/0044054 | A1 | 2/2013 | Lee et al. |
| 2014/0334671 | A1 | 11/2014 | Lee et al. |
| 2015/0042680 | A1 | 2/2015 | Grossinger |
| 2015/0310670 | A1 | 10/2015 | Grossinger |
| 2015/0317037 | A1 | 11/2015 | Suzuki |

FOREIGN PATENT DOCUMENTS

| | | |
|---|---|---|
| DE | 41 15 445 A1 | 1/1992 |
| EP | 0547599 B1 | 11/1997 |
| EP | 2166305 A1 | 3/2010 |
| JP | 2000-267800 | 9/2000 |
| KR | 10-2009-0084767 A | 8/2009 |
| WO | WO 2009/018161 | 2/2009 |
| WO | WO 2009/153446 A2 | 12/2009 |
| WO | WO 2011/036618 A2 | 3/2011 |
| WO | WO 2013/127974 A1 | 9/2013 |
| WO | WO 2014/083485 A1 | 6/2014 |

OTHER PUBLICATIONS

European Patent Office, Search Report and Opinion, European Patent Application No. 10818488.8, dated Jun. 30, 2015, eight pages.

International Search Report and the Written Opinion dated Jun. 16, 2011 From the International Searching Authority Re. Application No. PCT/IB2010/054228.

Japan Patent Office, Office Action, Japanese Patent Application No. 2012-530394, dated Jan. 15, 2016, six pages.

Kim, H. et al., "Diffractive Optical Element with Apodized Aperture for Shaping Vortex-Free Diffraction Image," Japanese Journal of Applied Physics, Dec. 2004, pp. 1530-1533, vol. 43, No. 12A.

Koninckx, T.P. et al., "Scene-Adapted Structured Light," 2005 IEEE Computer Society Conference on Computer Vision and Pattern Recognition, Jun. 20, 2005, pp. 611-618, vol. 2.

Korean Office Action (Notice of Preliminary Rejection), Korean Application No. 10-2012-7009974, dated May 12, 2016, 4 pages.

Notice of Reason for Rejection dated Mar. 7, 2014 From the Japanese Patent Office Re. Application No. 2012-530394 and It's Translation Into English.

Payeur, P. et al., Structured Light Stereoscopic Imaging With Dynamic Pseudo-Random Patterns, Jul. 6-8, 2009, Image Analysis and Recognition, $6^{th}$ International Conference, ICIAR, Halifax, Canada, pp. 687-696.

PCT International Search Report and Written Opinion, PCT Application No. PCT/IL2012/050523, dated May 27, 2013, 15 pages.

PCT International Search Report and Written Opinion, PCT Application No. PCT/US2016/023611, dated Jun. 17, 2016, 18 pages.

PCT International Search Report and Written Opinion, PCT/IL2014/050922, dated Feb. 17, 2015, 12 Pages.

Posdamer, J. L., "Surface Geometry Acquisition Using a Binary-Coded Structured Illumination Technique," Computers in Industry, vol. 3, No. 1-2, Mar. 1, 1982, pp. 83-92.

State Intellectual Property Office of the People's Republic of China, First Office Action, Chinese Patent Application No. 201480058469.9, dated Mar. 8, 2017, twenty pages.

Twardowski, P. et al., Three Dimensional Shape Measurement Based on Light Patterns Projection Using Diffractive Optical Elements; Proceedings of SPIE, vol. 7716, Apr. 30, 2010, pp. 77162I-77162I-8.

United States Office Action, U.S. Appl. No. 15/057,382, dated Jun. 17, 2016, 17 pages.

Weinmann, M. et al., A Multi-Camera, Multi-Projector Super-Resolution Framework for Structured Light, 2011 International Conference on 3D Imaging, Modeling, Processing, Visualization and Transmission, IEEE, May 16, 2011, pp. 397-404.

Canadian Intellectual Property Office, Office Action, Canadian Patent Application No. 2,924,622, dated Oct. 17, 2017, four pages.

United States Office Action, U.S. Appl. No. 15/077,540, dated May 23, 2017, 15 pages.

Australian Government, IP Australia, Examination report No. 1 for standard patent application, Australian Patent Application No. 2014338511, dated Jan. 17, 2018, four pages.

State Intellectual Property Office of the People's Republic of China, Third Office Action, Chinese Patent Application No. 201480058469.9, dated Feb. 7, 2018, twelve pages.

Canadian Intellectual Property Office, Office Action, Canadian Patent Application No. 2,924,622, dated Mar. 2, 2018, three pages.

* cited by examiner

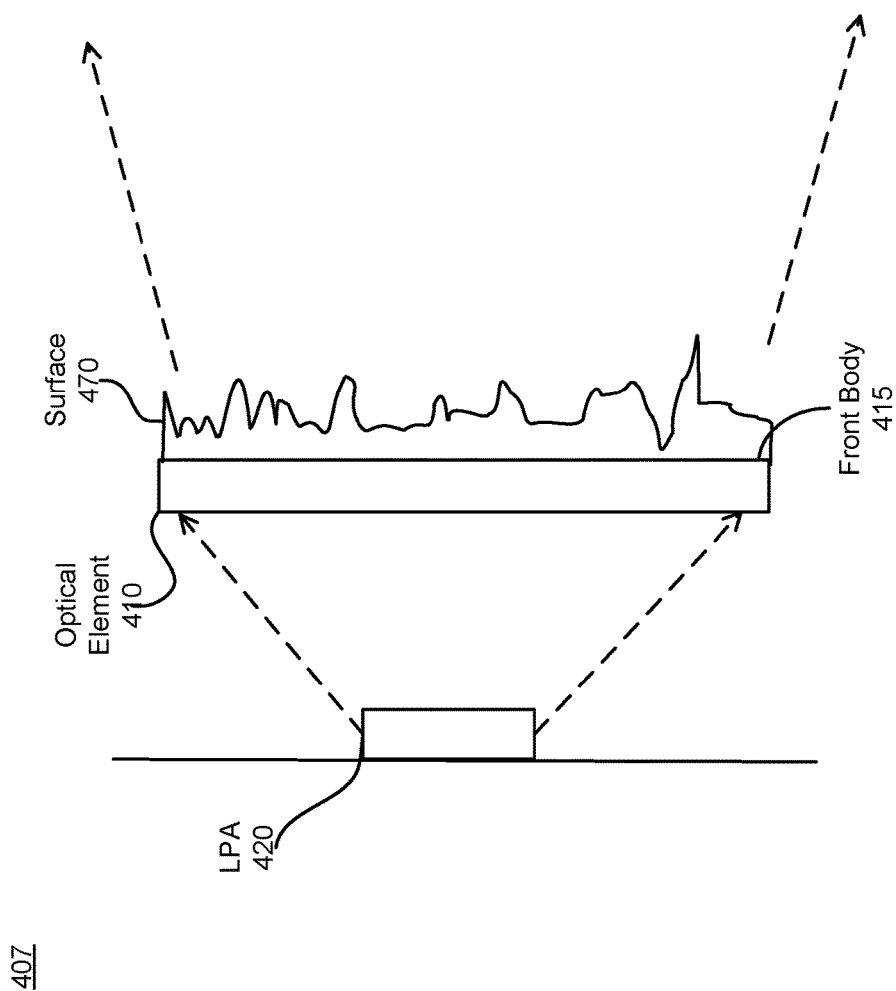

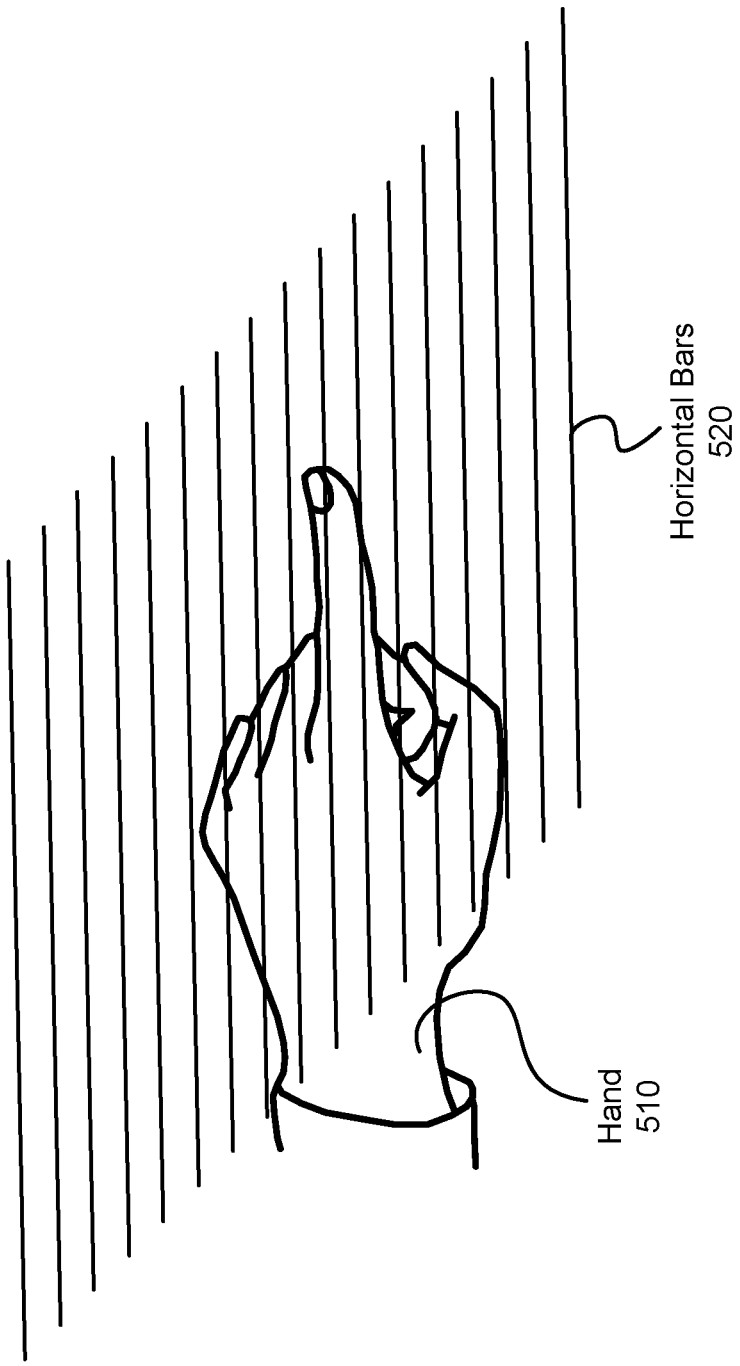

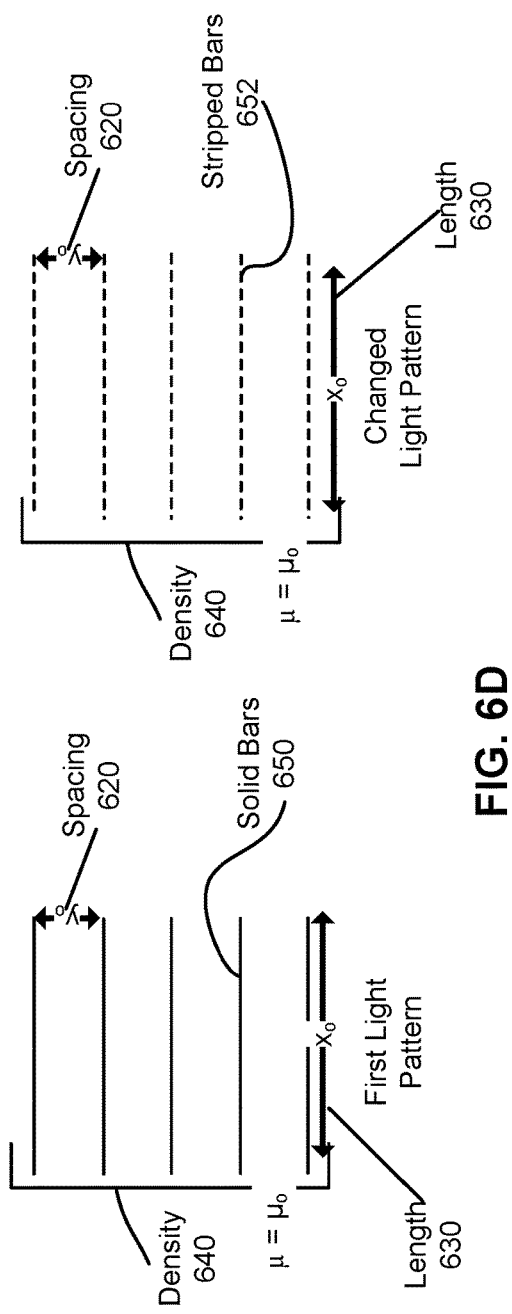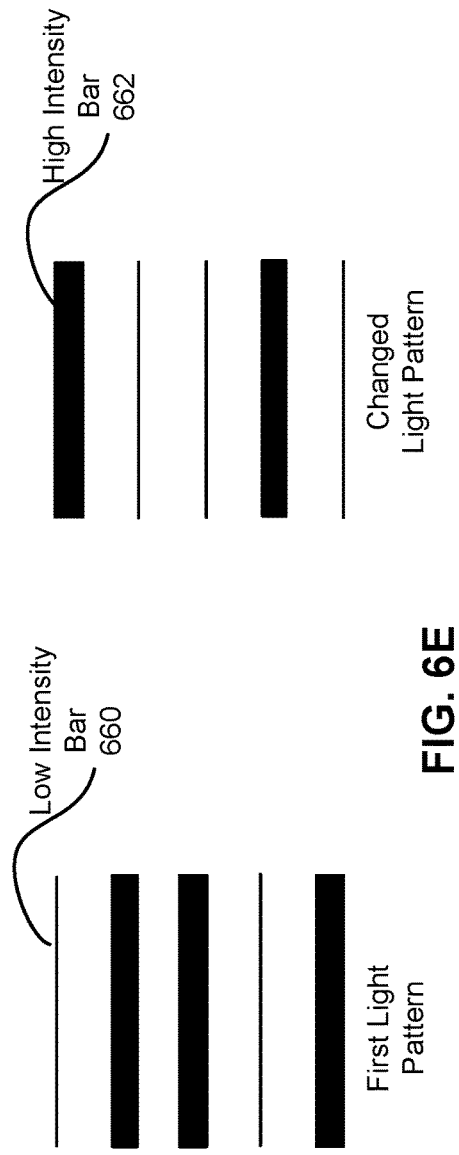
FIG. 6D
FIG. 6E

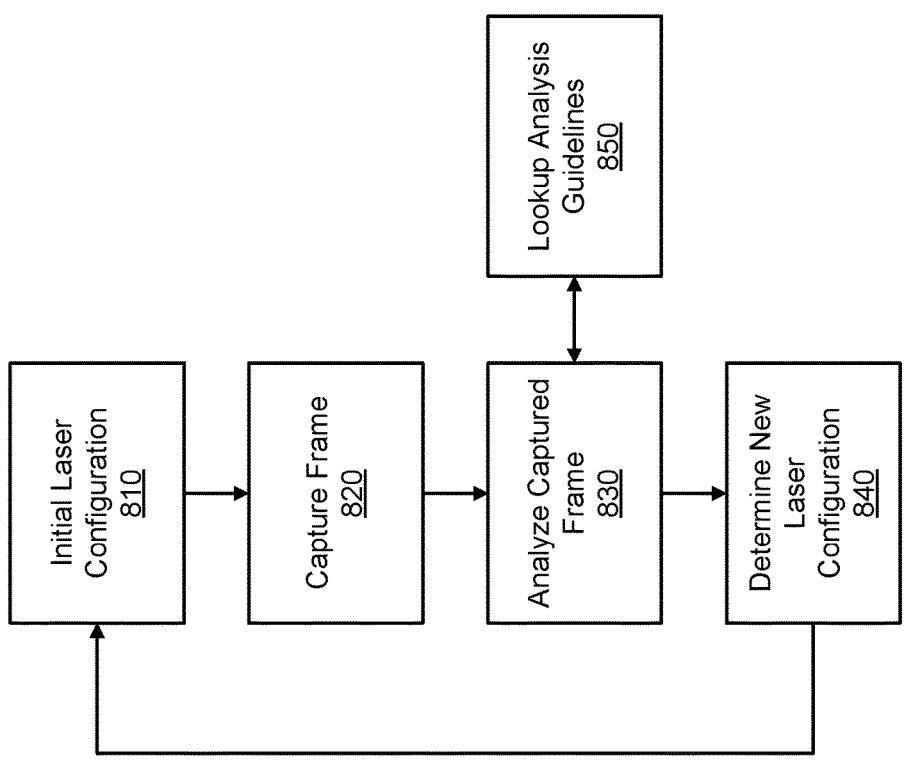

DEPTH MAPPING WITH A HEAD MOUNTED DISPLAY USING STEREO CAMERAS AND STRUCTURED LIGHT

CROSS-REFERENCE TO RELATED APPLICATION

This application is a continuation of U.S. application Ser. No. 15/077,540, filed Mar. 22, 2016, which claims the benefit of U.S. Provisional Patent Application No. 62/136,549, filed Mar. 22, 2015, the disclosure of which is hereby incorporated by reference in its entirety. Additionally, the following applications are hereby incorporated by reference as if fully set forth herein, namely U.S. patent application Ser. No. 13/497,589, filed on Sep. 19, 2010, International Patent Application No. WO2013/088442 filed Dec. 13, 2012, U.S. Provisional Patent Application No. 61/926,476, filed on Jan. 13, 2014, U.S. Provisional Patent Application No. 62/035,442, filed on Aug. 10, 2014.

BACKGROUND

The present disclosure generally relates to three-dimensional depth mapping using structured light, and more particularly, but not exclusively, to a system for tracking.

Tracking of styluses and fingers in a three-dimensional field in front of the computer is available and uses various tracking technologies. Tracking technologies may include, among others, visual and IR imaging and ultrasonics. The term 'tracking' may refer to following the positioning and motion of an object in three-dimensional space and includes processing of inputs received at a tracking computer in order to determine the position or motion. For example, in the case of a computer mouse, tracking may include processing the mouse outputs to determine motion. In the case of an object being followed visually, the term tracking may include image processing of successive frames capturing the object. One method of imaging simply uses cameras to view and process a scene. The cameras may follow specific marks that are placed in the scene or the imaging system can look for specifically recognizable features such as fingers. Drawbacks of such visual imaging include a requirement that the three-dimensional area is sufficiently illuminated. Furthermore, the only features that can be tracked are features that are recognized in advance, and motion tracking combined with feature recognition may not give accurate results. To overcome these problems, tracking using structured light was introduced.

In tracking using structured light, a known pattern of pixels is projected onto a local area in which tracking is to occur. The way that the pattern deforms on striking surfaces allows the vision system to calculate the depth and surface information of objects in the scene. Typical patterns used comprise of grids one or more structure light elements such as horizontal or vertical bars. In other embodiments, a structured light pattern may comprise of other regular geometric elements such as circles, triangles, angled bars, or any combination of thereof. Various devices use structured light patterns to enable the use of gesture recognition and 3D depth mapping. The structured light pattern transmitter includes a laser emitter and a diffractive optical element (DOE).

Projecting a narrow band of light onto a three-dimensionally shaped surface produces a line of illumination that appears distorted from other perspectives than that of the projector, and can be used for an exact geometric reconstruction of the surface shape.

A faster and more versatile method is the projection of patterns comprising of many bars at once, or of arbitrary fringes, as this allows for the acquisition of a multitude of samples simultaneously. Seen from different viewpoints, the pattern appears geometrically distorted due to the surface shape of the object.

Although many other variants of structured light projection are possible, patterns of parallel bars are widely used. The displacement of the bars allows for an exact retrieval of the three-dimensional coordinates of any details on the object's surface.

One known method of stripe pattern generation is the laser interference method, which utilizes two wide planar laser beam fronts. Interference between the beam fronts results in regular, equidistant line patterns. Different pattern sizes can be obtained by changing the angle between these beams. The method allows for the exact and easy generation of very fine patterns with unlimited depth of field. Disadvantages include the high cost of implementation, difficulties providing the ideal beam geometry, and laser typical effects such as speckle noise and the possible self-interference with beam parts reflected from objects. Furthermore, there is no means of modulating individual bars, such as with Gray codes.

Specifically, a disadvantage of using a single source emitter such as an edge emitter laser diode is the fact that the light pattern that it produces can be controlled only as a single unit. This means that while the light pattern can be entirely turned on, off or dimmed, it cannot be changed dynamically.

Structured light patterns may be constructed using invisible light such as infrared light. Alternatively, high frame rates may render the structured light imperceptible to users or avoid interfering with other visual tasks of the computer.

The vertical-cavity surface-emitting laser, (VCSEL) is a type of semiconductor laser diode in which laser beam emission is perpendicular from the top surface, as opposed to conventional edge-emitting semiconductor lasers, which emit from surfaces formed by cleaving the individual chip out of a wafer.

There are several advantages to producing VCSELs, as opposed to edge-emitting lasers. Edge-emitters cannot be tested until the end of the production process. If the edge-emitter does not function properly, whether due to bad contacts or poor material growth quality, the production time and the processing materials have been wasted. VCSELs can be tested at several stages throughout the process to check for material quality and processing issues. For instance, if the vias have not been completely cleared of dielectric material during the etch, an interim testing process may be used to determine that the top metal layer is not making contact with the initial metal layer. Additionally, because VCSELs emit the beam perpendicularly to the active region of the laser, tens of thousands of VCSELs can be processed simultaneously on a three-inch Gallium Arsenide wafer. Furthermore, even though the VCSEL production process is more labor and material intensive, the yield can be controlled to a more predictable outcome.

There is a significant advantage in that the use of VCSEL laser array for a structured light system, in that use of the array allows for a reduction in the size of the structured light transmitter device. The reduction is especially important for embedding the transmitter in devices with size restrictions such as a mobile phone or wearable devices.

However, despite the above advantages, the VCSEL array is not currently used for structured light scanning systems for a number of reasons. Many diffraction patterns require a coherent Gaussian shaped beam in order to create the high density patterns needed for high-resolution tracking. The VCSEL array merely provides multiple individual Gaussian beams positioned next to each other and usually with overlap between them. The multiple points and overlap between them reduce the detection performance in high-density areas in the light pattern and restrict the use of various diffractive design techniques that requires a pre-defined Gaussian beam. Such designs include a Top-Hat design, Homogeneous line generators and other complex high performance structures.

Indeed the problem with a standard diffractive design is that the entire VCSEL laser array is used as a single light source. Thus, when using a multiple spot design the array image is obtained for each spot instead of having a focused Gaussian beam. A diffractive design that requires a Gaussian beam as an input will not get the required output at all. The problem becomes more severe in dense light patterns, because in these light patterns, there is a need to focus the source beam onto a tiny spot in order to separate the features and this is not possible if the light source is an array of lasers.

SUMMARY

The present embodiments provide an array of lasers, such as a VCSEL laser array. Each individual laser of the laser array is modulated individually or in groups. The individual lasers or groups of lasers may be modulated statically or dynamically to generate and alter a structured light pattern as needed.

Each laser in the array or group of lasers being modulated together is provided with its own optical element. The optical element associated with an individual laser or group of laser is typically a diffraction element. The diffraction element may be individually controlled so that the overall structured light pattern can be selected for given circumstances and/or can dynamically follow regions of interest.

The present disclosure provides an apparatus for generating a structured light pattern. The structured light pattern is generated by an apparatus comprising an array of lasers arranged to project light in a pattern into a three-dimensional (3D) space and a plurality of optical elements. Each optical element defines an individual cell of the VCSEL laser array. Each cell is aligned with respective subsets of the VCSEL laser array. The optical element of each cell individually applies a modulation to light passing through the optical element to generate a distinguishable part of the structured light pattern. In an embodiment, a laser emitter or an array of laser emitters is grouped into a number of subsets of laser emitters, such as rows or columns of laser emitters which may be switched on or off independently, by a suitable driver, thus creating a modifiable pattern. In another embodiment, the switchable subsets of laser emitters can be collected into two switchable groups of even and odd rows.

Optical modulation may comprise any of a diffractive modulation, refractive modulation, or some combination of a diffractive and a refractive modulation. In an embodiment, the optical elements and the subset of the array of lasers comprising a respective cell are constructed from a single molded element. In an embodiment, a width of the cell is 1 mm or less. In still another embodiment, the width of the optical element is 1 mm or less and the cells are individually controllable to change the diffractive modulation.

The cells may be configured to dynamically change the generated structured light pattern based on receiving one or more instructions from an external control or a processor. That is to say, one or more diffraction properties associated with a cell may be dynamically changed according to received data. A captured frame comprising a plurality of pixels from a local area may be analyzed and a new laser configuration may be reached to optimize tracking. In an embodiment, the cells associated with a structured light emitter are further controllable with respect to the position and shape of the generated structured light element. In an embodiment, the dynamic control is configurable to apply increased resolution of the structured light pattern to parts of the scene to apply reduced resolution of the structured light pattern to other parts of the scene. In other embodiments, the dynamic changes to the structured light pattern comprise changes to orientation of the structured light pattern or structured light elements comprising the structured light pattern. The dynamic changes to the structured light pattern may result in a change in one or more cells, in a cellwise manner, associated with a light array. That is, the dynamic change in a projected and/or generated pattern is associated with a corresponding change in particular cell in a plurality of cells. The changes may be one or more of a change in optical functions including emission intensity, polarization, filtering parameters, and focus.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

FIG. 4C depicts a SLE for shaping an incident optical beam, according to an embodiment.

FIG. 5A shows a hand being tracked by a light pattern comprising a plurality of horizontal bars orientated parallel to the hand, in accordance with an embodiment.

FIG. 6D shows a change in shape of a projected pattern, in accordance with an embodiment.

FIG. 6E shows changes in intensity, in accordance with an embodiment.

FIG. 8 is a simplified flow diagram illustrating a procedure for modifying the pattern in one or more cells in accordance with an embodiment.

The figures depict embodiments of the present disclosure for purposes of illustration only. One skilled in the art will readily recognize from the following description that alternative embodiments of the structures and methods illustrated herein may be employed without departing from the principles, or benefits touted, of the disclosure described herein.

DETAILED DESCRIPTION

Figure 1:
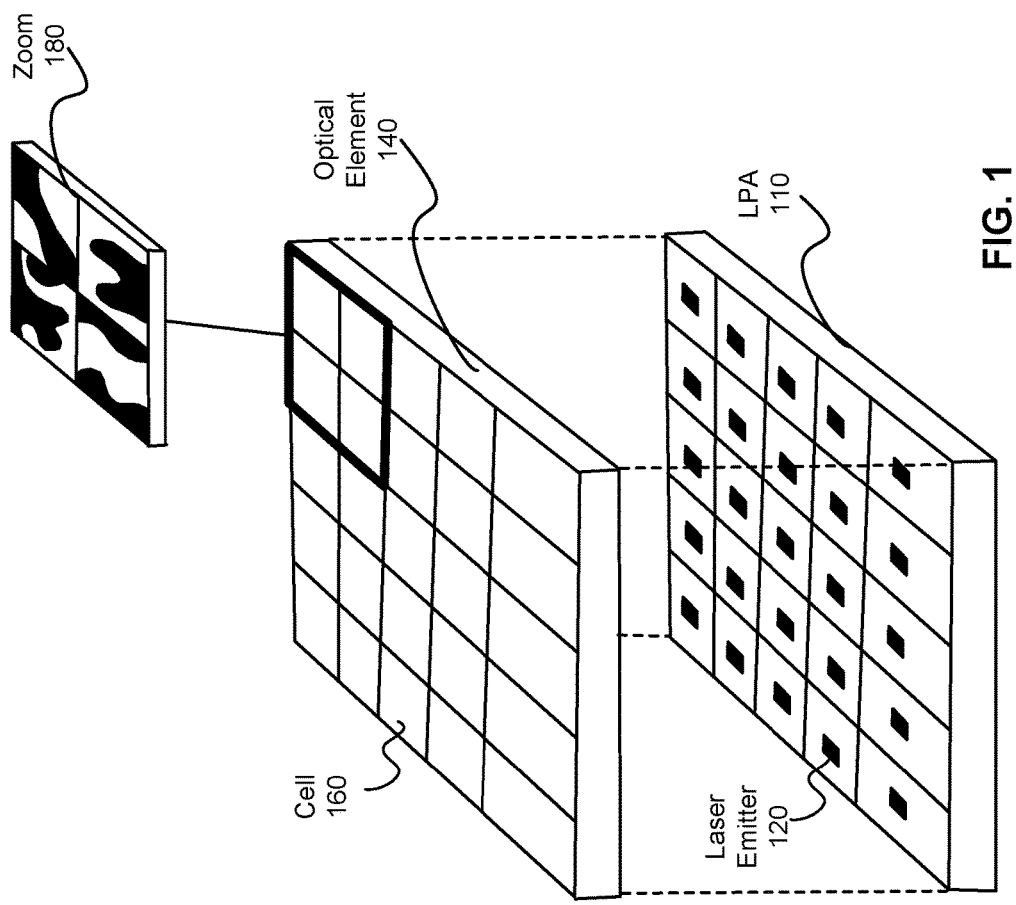
FIG. 1 is a schematic diagram of a structured light emitter (SLE) for 3D tracking using patterned light according to an embodiment.

FIG. 1 is a schematic diagram of a structured light emitter (SLE) 100 for 3D tracking using patterned light according to an embodiment. The SLE 100 includes a light producing array (LPA) 110 configured to emit patterned light such as structured light. In one or more embodiments, the LPA 110 is an array of lasers comprising a plurality of light sources such as laser emitters 120. The SLE 100 also includes an optical element 140. In various embodiments, the optical element 140 comprises a plurality of cells 160. Each cell 160 is configured as a diffractive element and is aligned with a particular laser emitter 120, so that individual cells of the plurality of cells 160 modulate the light emitted by a respective laser emitter 120. Zoom 180 of the cells 160 shows four cells 160 each with a unique diffractive pattern. The SLE 100 may generate a structured light pattern from the LPA 110. In one or more embodiments, the generated structured light pattern is projected into a 3D space for tracking objects and parts of a local area within that space. As used herein, a generated pattern is assumed to be associated with a structured light pattern.

The LPA 110 may generate multiple Gaussian shaped beams with overlap, which reduce the detection performance in high-density areas in the generated light pattern and restricts the use of various diffractive design techniques that require a pre-defined Gaussian beam. For example, diffractive design techniques may include a Top-Hat design, Homogeneous line generators, and other complex high performance structures. The LPA 110 may comprise one or more laser emitters 120. A laser emitter 120 may be a VSCEL laser configured to emit a Gaussian laser beam in the infrared (IR), visible (RGB), or ultra violet (UV) segments of the electromagnetic spectrum.

The LPA 110 may be configured with an external controller (not shown) such that each laser emitter 120 in the LPA 110 may be operated individually or in groups. For example, the individual laser emitters 120 are modulated statically or dynamically to provide and alter an emitted light associated with a particular laser emitter 120 as needed. A significant advantage may be gained through the use of a LPA 110. For example, the use of a LPA 110 comprising individual laser emitters 120 would reduce the size of the SLE 100 allowing the SLE 100 to be embedded in devices with size restrictions such as mobile phones or other wearable devices.

Each laser emitter 120, or group of lasers emitters 120, being modulated together, may be aligned with one or more cells 160 associated with the optical element 140. For example, light generated by a laser emitter 120 passes through a cell 160 and the cell 160 is configured to apply diffractive modulation to light passing through so that each subset of cells 160 provides a distinguishable part of the structured light pattern (a pattern). In various embodiments, the optical element 140 is positioned on the surface adjacent to the SLE 100 such that the plane of the optical element 140 is parallel to that of the LPA 110. In other embodiments, the width of the optical element 140 is 1 millimeter or less.

It is important to note that a subset as used herein is comprises one member of a group, pairs of, triplets, combinations of, and dynamically changing combinations of cells 160 and associated laser emitters 120. In one or more embodiments, each group of lasers is independently switchable. That is, each subset of cells and associated laser emitters may be independently controllable by a controller further described below in conjunction with FIG. 3.

As depicted in FIG. 1, the surface of the optical element 140 may be divided into one or more of cells 160. Each cell 160 in optical element 140 represents an area that may be positioned above a single laser emitter 120 or a sub-group of laser emitters 120 that are controlled together via an external controller (not shown). It should be noted that, the laser emitters 120 in the group or subgroup are controlled together, separately from laser emitters 120 in other groups or subgroups.

The cell 160 associated with the optical element 140 is a controllable optical diffraction element. That is, a unique diffractive pattern may be designed for each cell 160. In some embodiments, the cell 160 comprises a refractive optical element or some combination of refractive and diffractive optical elements. In one or more embodiments, each cell individually applies a diffractive modulation to the generated light passing through it.

In an embodiment, the width of a cell 160 is 1 millimeter or less. The cells 160 of the optical element 140 can be individually controlled both dynamically and statically by an external controller (not shown). Such a configuration of cells 160 may provide different light patterns at different parts of the array so that the overall structured light pattern can be selected for given circumstances and/or can dynamically follow regions of interest. Light patterns generated by a cell 160 may include structures such as bars, grids and dots and will be discussed in greater detail below in conjunction with FIGS. 2A-2D and FIGS. 6A-6E. In the following, the term 'cell' relates to a surface operable with a single laser operable or any group of laser emitters 120 that are operated together to provide a particular part of a projected pattern. The structure and dynamic control of a cell 160 are further described below. In the interest of convenience, diffractive optical elements are understood to mean, herein, diffractive optical elements, refractive optical elements, or any combination of diffractive and refractive optical elements.

A unique diffractive pattern may be designed for each cell 160, thus enabling the creation of any part of a structured light pattern. For example, a diffractive pattern that may be generated by a cell 160 comprises light generated by a laser emitter 120 passing through the diffractive pattern of a cell 160. Zoom 180, shows a group of four cells 160 wherein the light parts represent refractive elements, while the dark parts represent diffractive elements. The light passing through the diffractive pattern of a cell 160 may generate a sub-pattern of the structured light and the overall pattern, may be formed from the patterns produced by light passing through each individual cell 160. For example, the overall pattern is produced by tiling, overlapping, or other ways for positional of individual features generated by a cell 160 or a subset of cells 160 associated with the optical element 140.

The diffractive pattern of a cell 160 is determined by a combination of at least two optical functions. In one or more embodiments the first optical function is a positioning function that determines the position of the light feature in the entire structured light image and may utilize one or more optical elements to direct light. For example, a positioning function utilizes a prism blazed grating to change the path of the light emitted by the associated laser emitter 120 and subsequently passing through the cell 160. A second, optical function, may relate to the shape of the generated light feature. By way of example, such optical functions include line generators, a multi spot pattern, or other features including sub features of the generated light pattern.

Additional optical functions may also be associated with cells 160. These additional optical functions include intensity, focal length, polarization, and phase. The optical functions listed above are not an exhaustive list and other types of optical functions will be apparent those skilled in the art. It should also be noted that an optical function listed above or a combination of optical functions may be implemented by one cell 160 or a combination of cells 160 associated with an optical element 140.

Depending on the designed position of the optical element 140 comprising cells 160 relative to the LPA 110, any pattern may be generated. For example, adjacent-Gaussian beams generated by one or more laser emitters 120 are combined to avoid the as a single light source perspective. In another embodiment, the cell 160 may generate a dynamic pattern by modulating the combination of one or more optical functions associated with one or more cells 160. For example, each cell 160 can be controlled individually controlled by modulating the current or voltage waveform applied to it. In one or more embodiments, a current or voltage waveform is received from an external controller (not shown) such as a processor associated with a mobile device. External controller or processors are further described, below, in conjunction with FIG. 3.

In various embodiments, cells 160 are configured to be controlled dynamically to provide changes to the generated structured light pattern. For example, a cell 160 may be dynamically controlled to change the diffractive pattern of a cell 160. In various embodiments, the generated pattern may be changed to increase or decrease resolution in various parts of a scene. For example, the pattern may change to increase resolution based on a determined level of interest being high. Alternatively, if the determined level of interest is low, the generated pattern may be changed to decrease resolution. In other embodiments, a generated pattern may be changed to increase or decrease at least one of intensity, polarization, density, focal length, filtering parameters, or any other feature of light apparent to those skilled in the art. The dynamic changes to one or more cells 160 comprise a cellwise change. That is, the dynamic change in a projected and/or generated pattern is associated with a corresponding change in a particular cell. Patterns that may be generated by a SLE 100 are further described below in conjunction with FIGS. 6A-E.

It should be noted that, different parts of a pattern may be, momentarily changed in order to provide additional details regarding triangulation and depth estimation based on a determined level of interest. That is, the cell 160 may be dynamically changed according to received data associated with a frame captured with an initial configuration of LPA 110. For example, a frame comprising a two-dimensional (2D) array of pixels is captured using an initial configuration of LPA 110. The received frame is analyzed and a processor (not shown) which may determine a news initial LPA 110 configuration. This new LPA 110 configuration becomes the new initial LPA 110 configuration for the next stage as the cycle continues. An example is illustrated and discussed below in conjunction with FIG. 8.

In one embodiment, the intensity of the generated light pattern is typically changed. The intensity of a generated pattern may be changed over part or all of the generated light pattern. For example, parts of the local area may be brightly lit by incident light while other parts of the local area are dimly lit. In the example above, high intensity light may be aimed at the brightly lit parts and low intensity light may be aimed at the dimly lit regions of the local area. Other forms of intensity modulation may include switching one or more cells 160 associated with a LPA 110 or one or more subsets of laser emitters 120 associated with a cell 160 into on or off states simultaneously or successively. In various embodiments, modulation of a generated light pattern is employed to save power.

In other embodiments, the density or orientation of the generated may be changed to provide a different view of the local area in order to enable accurate tracking and depth perception of an object. In the particular example of orientation, a feature of the local area may be more effectively illuminated in a given orientation. Additional light patterns are discussed in further detail below in conjunction with FIGS. 5 and 6.

FIGS. 2A-2D illustrate each a simplified schematic diagram depicting various embodiments of SLE 200 generating a light pattern onto a local area in accordance with an embodiment. SLE 200 is an embodiment of SLE 100 described above in conjunction with FIG. 1 and comprises a plurality of cells 211-219 including a LPA 110, and an optical element 140. In FIGS. 2A-2D, the SLE 200 includes nine distinct cells (e.g., cells 211-219) wherein each cell 211-219 is an embodiment of cell 160 as described above in conjunction with FIG. 1. That is, each SLE 200 includes an LPA 110 comprising one or more laser emitters 120 aligned with corresponding cells 211-219. In other embodiments, SLE 200 may comprise more or fewer cells than those depicted herein.

Figure 2A:
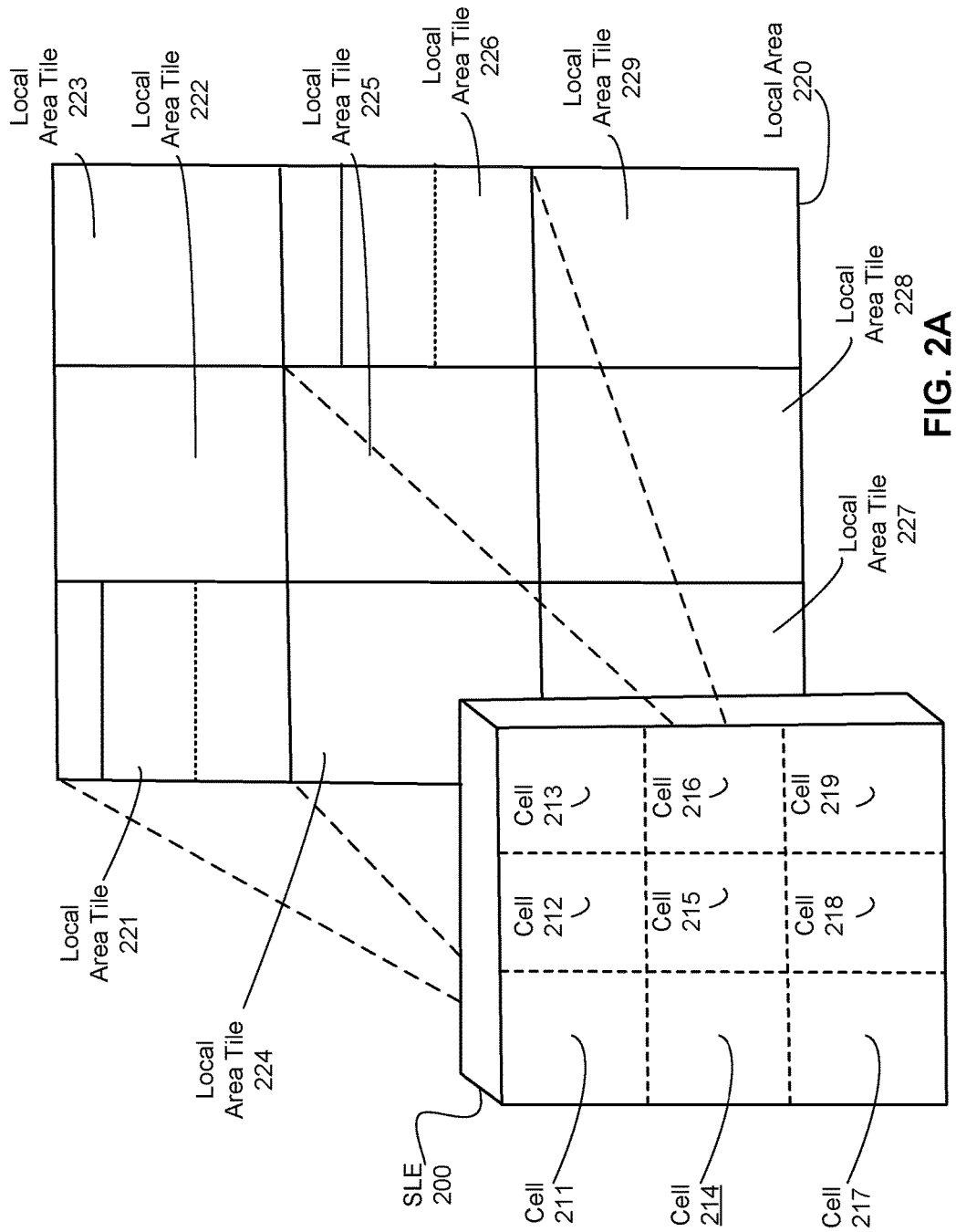
FIG. 2A depicts an SLE illuminating a local area with one or more patterns of light, according to an embodiment.

FIG. 2A depicts the SLE 200 illuminating a local area with one or more patterns of light, according to an embodiment. The SLE 200 comprises an LPA (e.g., LPA 110) and an optical element (e.g., the optical element 140), according to an embodiment. As described above in conjunction with FIG. 1, the LPA 110 comprises one or more laser emitters 120 wherein each laser emitter 120 is coupled to a corresponding cell (e.g., one of cells 211-219). Each cell 211-219 illuminates different local area tile (e.g., local area tile 221-219) of local area 220 in a forward projection. For example, cell 211 illuminates local area tile 221. Similarly, cell 219 illuminates local area tile 229. It should be noted that in local area 220, each local area tile (e.g., 221-229) has a different pattern. In various embodiments, all local area tiles 221-219 merge together to form a complete light pattern.

Cells 211-219 are aligned with laser emitters 120 comprising the SLE 100. Each cell 211-219 individually applies a diffractive modulation to the light passing through the cell such that each cell 211-219 projects a distinguishable part of the structured light medium. The cells may be individually controlled in order to change their diffractive modulation. Therefore, different parts of the generated pattern may be different or the different parts of the scene may contain a different density of structured light elements. Each cell 211-219 and respective laser emitter (not shown) together project light onto a corresponding local area tile. For example, a cell 211 projects a light pattern on local area tile 221 comprising three horizontal bars and cell 219 does not illuminate adjacent local area tiles 222, 224, and 225. Similarly, a cell 216 projects a light pattern on local area tile 226 comprising three horizontal bars and cell 216 does not illuminate adjacent local area tiles 222, 223, 225, 228, and 229. All the projected tiles (e.g., local area tile 221-220) merge together to form a complete light pattern on local area 220. In FIG. 2A patterns on local area tiles 221 and are illustrated, and the patterns on the remaining local area tiles are omitted for simplicity.

Figure 2B:
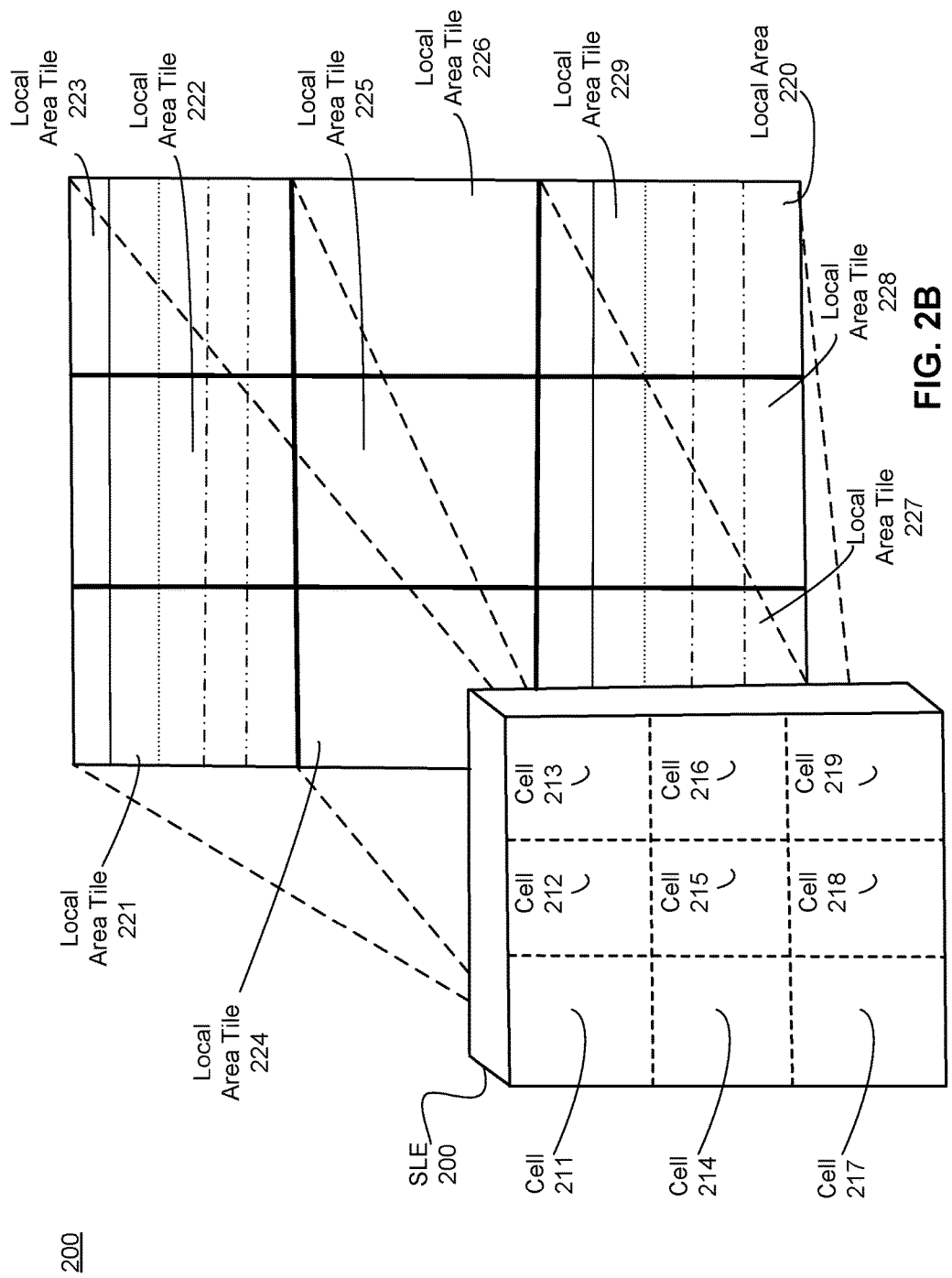
FIG. 2B illustrates a simplified schematic diagram of the SLE depicted in FIG. 2A in which a cell comprises two or more laser emitters, specifically three in the case illustrated, according to an embodiment.

FIG. 2B illustrates a simplified schematic diagram of the SLE 200 depicted in FIG. 2A in which a cell 211-219 comprises two or more laser emitters. In FIG. 2B, the SLE 200 is configured to project a pattern on a local area 220. The pattern projected by SLE 200 represents a variation of the projected pattern of FIG. 2A and is formed by tiling the individual patterns produced by cells 211-219 on local area tiles 221-229. Cell 211 illuminates local area tile 221 while cell 213 illuminates local area tile 223. Similarly, cells 214 and 216 illuminate local area tiles 224 and 226 respectively. In FIG. 2B, each cell 211-219 illuminates a different triplet of local area tiles 221-219. A triplet is a row of local area tiles 221-229 that share a pattern. As illustrated in FIG. 2B, local area 220 comprises a set of three triplets. For example, local area tiles 221-223 comprise one triplet, local area tiles 224-226 comprise another, and local area tiles 227-229 comprise a third. Local area tiles 221-229 in a triplet share different patterns than those local area tiles in adjacent triplets. For example, local area tiles in the first triplet 221-223 comprise a pattern of two solid horizontal bars each separated by a dotted horizontal bar while local area tiles comprising the second triplet, local area tile 224-227 containing no bars. In various embodiments, the combination of one or more triplets of local area tiles 221-219 comprise one complete pattern.

Figure 2C:
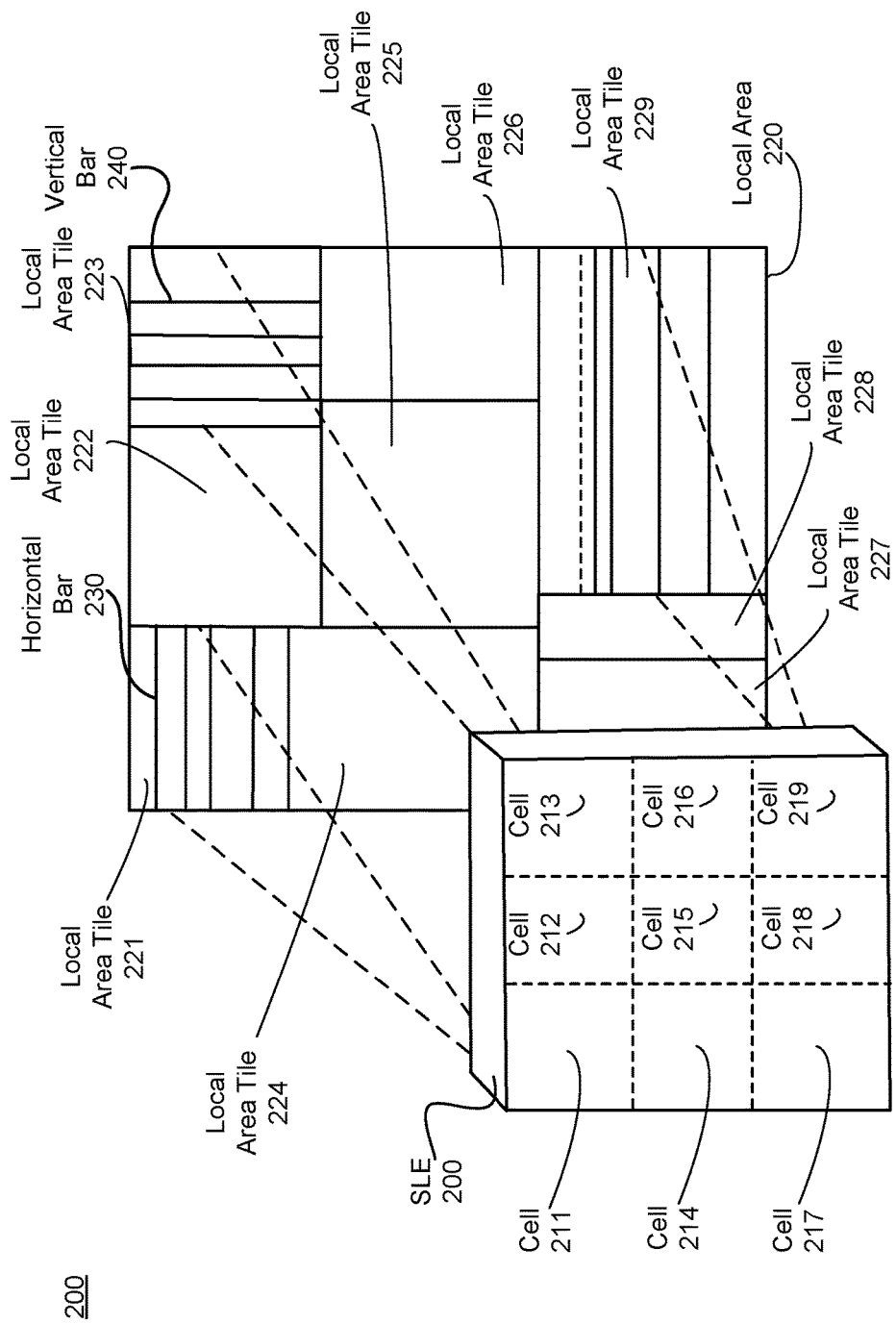
FIG. 2C illustrates a simplified schematic diagram of the SLE depicted in FIG. 2A in which different cells have different designs and different orientations, according to an embodiment.

FIG. 2C illustrates a simplified schematic diagram of the SLE 200 depicted in FIG. 2A in which different cells have different designs and different orientations. The SLE 200 of FIG. 2C is configured to project a light pattern on a local area 220. The projected light pattern may comprise one or more light patterns projected by cells 211-219. It should be noted that different cells 211-219 have different designs and different orientations such as horizontal 230 and vertical bars 240. In FIG. 2C each cell 211-219 illuminates one or more local area tiles 221-229 in local area 220.

Cells 211-219 may project a light pattern on local area 220 of variable sizes, including aspect ratios. In FIG. 2C, the local area 220 includes a light pattern comprising squares and rectangles of various sizes. In various embodiments, regardless of the dimensions of the individual local tiles 221-229, the area of the local area 220 is held constant. By way of example, if the area of a particular local area tile 229 is expanded the area of one or more of the other local area tiles 221-228 is, proportionately decreased such that the total area of local area 220 is maintained. Alternatively, if the area of a particular local area tile 221-229 is decreased, the area of one or more of the remaining local area tiles 221-219 in a local area 220 is proportionately increased. For example, large rectangular local tile 224 causes a reduction in the area of the square tile 221. Similarly, for example, the large rectangular local tile 225 results in a change in the size and aspect ratio of local area tile 226 such that local area tile 226 forms a small rectangle. Additionally, a cell 211-219 may vary the orientation of an illuminated local area tile 221-229 by rotating the tile by a set number of degrees. In some embodiments, the required tile sizes, aspect ratios, and orientations is calculated in real-time by a processor (not shown) and an imager (not shown). The processor and imager are further described below.

Figure 2D:
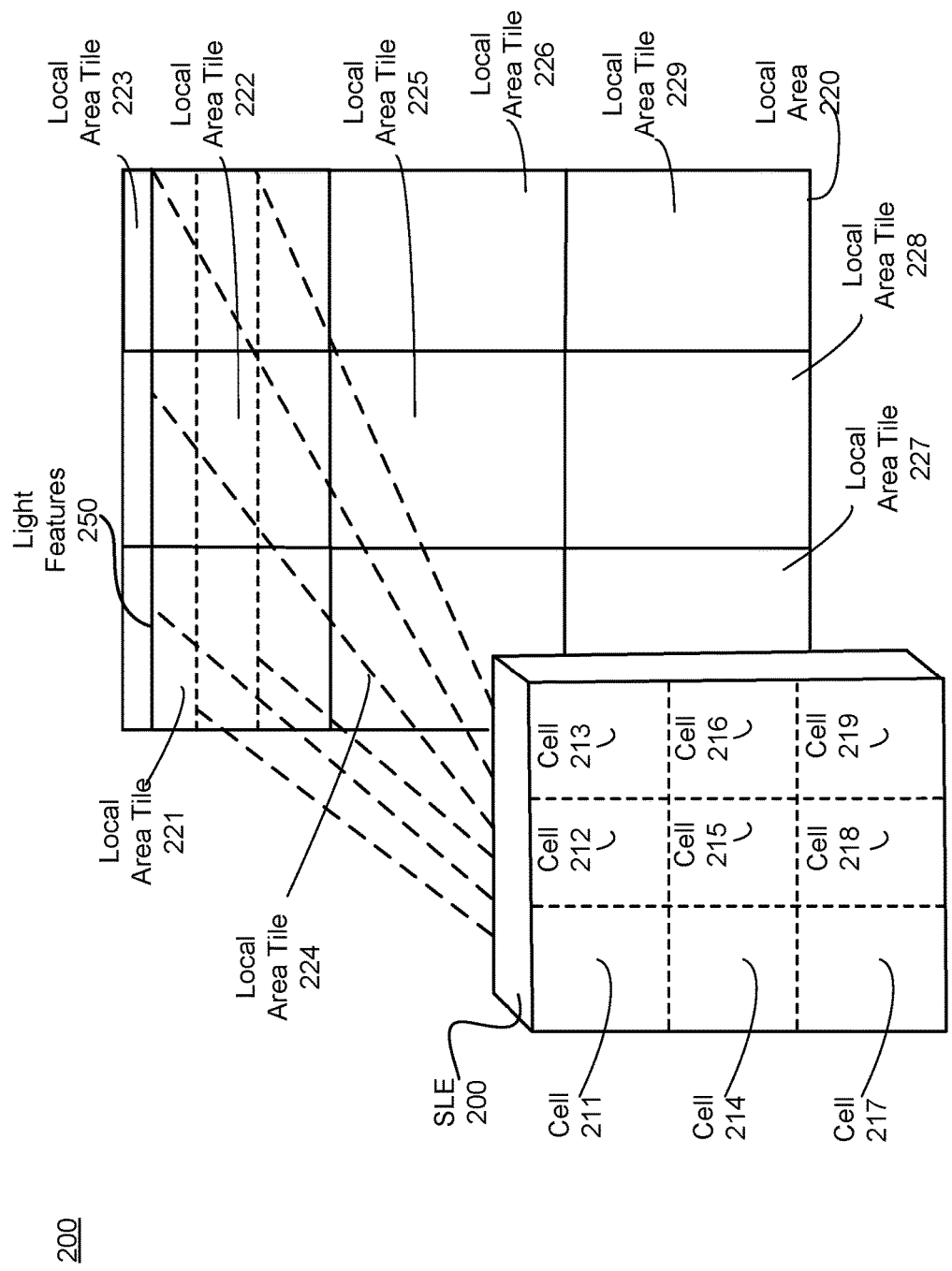
FIG. 2D illustrates a simplified schematic diagram of SLE depicted in FIG. 2A in which in which each cell is responsible for producing various light features of the pattern that are not necessarily organized in separate tile structures, according to an embodiment.

FIG. 2D illustrates a simplified schematic diagram of SLE 200 depicted in FIG. 2A in which in which each cell is responsible for producing various light features of the pattern that are not necessarily organized in separate tile structures. The SLE 200 of FIG. 2D is configured to project a pattern on a local area 220 such that the patterns projected by the different cells 211-219 have different designs. In FIG. 2D, each cell 211-219 is configured to illuminate one or more local area tiles 221-229 with light features 250. FIG. 2D shows local area tiles 221-223 illuminated with light features 250 comprising one solid horizontal bar and two dashed horizontal bars while local area tiles 224-229 are blank. In some embodiments, the light features may be any number of horizontal bars, veridical bars, or other shapes (e.g., an irregular polygon). Additional light features are described below in conjunction with FIG. 6. It should be noted that in other embodiments the patterns projected may have different designs, different orientations, or any combination thereof.

Figure 3:
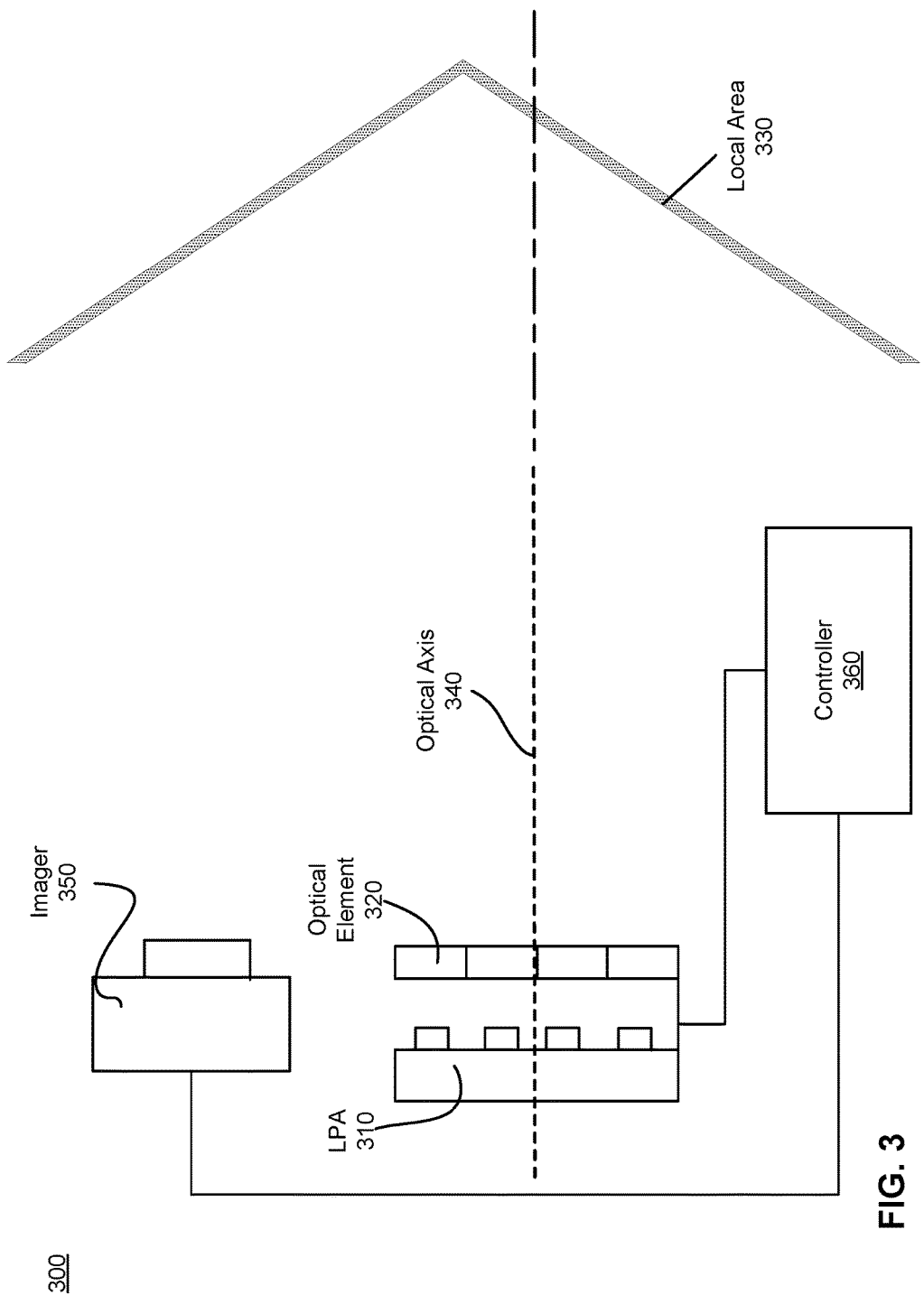
FIG. 3 is a simplified schematic diagram that illustrates an exemplary tracking system according to an embodiment.

FIG. 3 is a simplified schematic diagram that illustrates an exemplary tracking system 300 according to an embodiment. The tracking system 300 tracks one or more objects in a local area 330. The tracking system 300 comprises an LPA 310 to generate laser light, an optical element 320 to modulate the generated laser light and illuminate a local area 330. The LPA 310, optical element 320, and local area 330 are arranged along an optical axis 340. In some embodiments, the LPA 310 and optical element 320 are associated with an embodiment of SLE 100. FIG. 3 also comprises an imager 350 for tracking information about the local area 330 and providing feedback to a controller 360. The controller 360 receives data from the imager 350 and generates voltage and/or current waveforms to the LPA 310 and optical element 320 to illuminate the local area 330.

The LPA 310 and optical element 320 are embodiments of LPA 110 and optical element 140. In various embodiments, the LPA 310 generates a coherent optical beam in ranges of wavelengths of light (i.e., "bands of light). Example bands of light generated by the LPA 310 include a visible band (~380 nm to 750 nm), an infrared (IR) band (~750 nm to 1500 nm), an ultraviolet band (1 nm to 380 nm), or another portion of the electromagnetic spectrum of some combination thereof. The generated laser light may then be transmitted to the local area 330 via the optical element 320, which modulates the laser light generated by the LPA 310. In various embodiments, the LPA 310 and optical element 320 are configured to project the generated laser light and the generated laser light is projected onto local area 330. The modulated laser light illuminates all or part of a 2D or 3D local area 330. For example, the LPA 310 comprises of an array of VCSEL lasers that generate a Gaussian laser beam, which is subsequently modulated by the optical element 320 and illuminates a local area 330. In one or more embodiments, the modulated laser represents a set of horizontal bars, vertical bars, or regular geometrical shape. Embodiments of the LPA 310 and optical element 320 are further described above in conjunction with FIGS. 1 and 2.

Any particular cell associated with an optical element 320 may allow the position, the phase, the focus, the shape, the intensity, or the polarization of the generated beam to be modified. The above is not an exhaustive list and other modifications will be apparent to those skilled in the art. Additionally the optical functions may be utilized by a single optical element or by multiple optical elements as described further below in conjunction with FIG. 4.

The imager 350 is configured to monitor all or part of the local area 330. In various embodiments, the imager 350 monitors the local area 330 and captures one or more frames of the local area 330. The imager 350 may be a digital camera configured to capture one or more digital frames or any imagery sensor such as a complementary metal oxide silicon (CMOS) array. For example, the imager 350 is a digital camera configured to capture still frames or a digital video camera configured to capture a sequence of one or more frames of local area 330. In various embodiments, the imager 350 captures frames in a visible, IR, UV, or some combination thereof, and transmits the captured one or more frames to controller 360. It should be noted that in various embodiments, the imager 350 is configured to capture one or more frames in the same electromagnetic band as that in which the LPA 310 is operating. That is, if the LPA 310 is projecting a pattern in the IR band, the imager 350 is configured to also capture framers in the IR band. In some embodiments, the captured frames may be transmitted to the controller 360 in a file format, which represents a standardized means of organizing and storing digital images. For example, the captured frames may be transmitted as a Joint Photographic Experts Group (JPEG) file, a bitmap (BMP) file, or a potable network graphics (PNG) file. In another example, the imager 350 transmits a series of captured frames in a suitable video file format. In various embodiments, the image frames generated by the imager 350 comprise data in an uncompressed, compressed, or a vector format. The one or more frames captured by the imager 350 are transmitted to the controller 360.

The controller 360 is connected to both the imager 350 and the LPA 310. The controller 360 may be configured to generate voltage or current waveforms to modulate light produced by the LPA 310. In an embodiment, the current or voltage waveforms generated by controller 360 are one or more instructions to modulate the light produced by the LPA 310 and the controller 360 is configured to transmit instructions to the LPA 310. For example, the controller 360 may comprise a current source, a voltage source, and an electronic filter configured to control one or more lasers associated with the LPA 310. In other embodiments, the controller 360 may also be configured to dynamically control the optical element 320 including one or more cells 160 comprising the optical element 320. For example, the controller 360 may provide instructions to the LPA 310 including the optical element 320 to illuminate the local area 330 with a pattern comprising one or more vertical bars, one or more horizontal bars, or any other shape capable of being produced by the optical element 320 by diffracting light produced by lasers associated with the LPA 310. In one or more embodiments, instructions to the optical element 320 comprise instructions to one or more subsets of cells 160 associated with the optical element 320. Thus, cells associated with the optical element 320 may be dynamically controlled to provide changes to a structured light pattern In still other embodiments, the controller 360 may provide instructions to the LPA 310 and optical element 320 to alter one or more optical functions associated with the pattern generated by the optical element 320. For example, the controller 360 may provide instructions to the LPA 310 to independently control one or more subsets of laser emitters associated with the LPA 310. It should be noted that a subset of LPA 310 comprises two or more laser emitters 120. In an embodiment, a subset of the LPA 310 comprising two or more laser emitters including respective cells 160 and optical element 320 are constructed from a single molded element.

The controller 360 may be an external controller, or a digital processor such as a mobile phone, configured to perform one or more processes associated with tracking and performing light modulations in order to improve tracking. For example, the controller 360 provides instructions to modify one or more optical functions associated with the light pattern produced by the LPA 310 including the optical element 320. In an embodiment, the controller 360 is configured to receive frames from the imager 350, analyze the received frames and transmit one or more instructions to the LPA 310 and optical element 320 to modulate the illuminated local area accordingly. Instructions to modify the produced pattern may comprise directing, focusing or shaping the produced pattern in order to improve tracking. In other embodiments, the processor may provide instructions to one or more subsets of the LPA 310 to switch into an on or off state simultaneously, successively, or in coordination with an imager 350. The steps of receiving, analyzing, and transmitting are further described below in conjunction with FIG. 8.

Figure 4B:
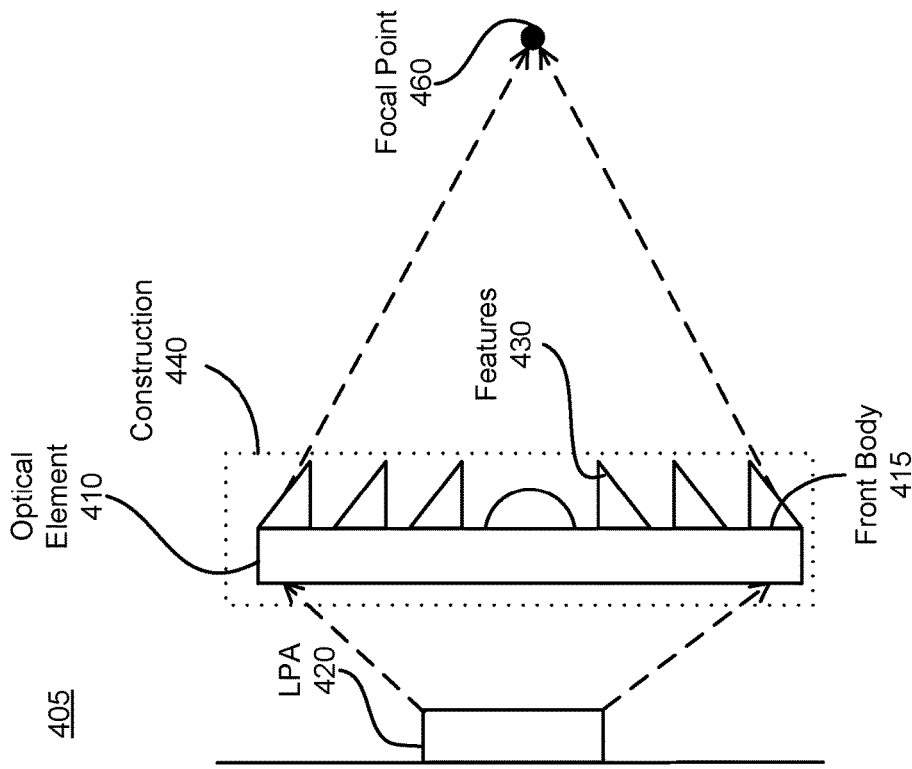
FIG. 4B depicts a SLE comprising an optical element for focusing an incident optical beam, according to an embodiment.
Figure 4A:
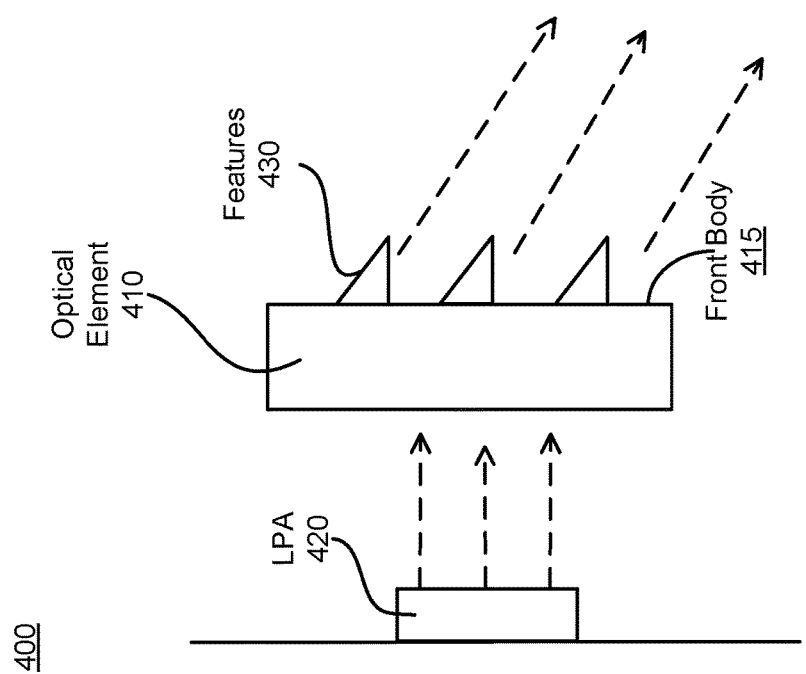
FIG. 4A illustrates a SLE comprising an optical element, LPA, and features for directing a light beam in a particular direction, according to an embodiment.

FIG. 4A illustrates a SLE 400 comprising an optical element 410, LPA 420, and features 430 for directing a light beam in a particular direction, according to an embodiment. SLE 400 is an embodiment of SLE 100 and LPA 420 and optical element 410 represent embodiments of LPA 110 and optical element 140, respectively. As shown in FIG. 4A, the optical element 410 directs an incident optical beam generated by LPA 420 via one or more features 430 protruding from optical element 410. The incident optical beam reflects off a plurality of features 430 emerging from a front body 415 of the optical element 410. In an embodiment, the reflection of light off one or more features 430 causes the change in direction of the light beam. In other embodiments, and depending on the arrangement of features 430, light may be directed due to refraction, diffraction or a combination of refraction and diffraction. It should be noted that in some embodiments, the optical element 410 is an embodiment of optical element 140 and comprises one or more cells 160 configured to reflect, diffract, refract, an incoming light beam generated by the LPA 420. In other embodiments, the cells 160 associated with the optical element 410 perform a combination of reflection, diffraction, refraction of the incoming light beam. In FIG. 4A, a saw tooth configuration of the features 430 in which tooth-like shapes have a downwardly sloping upper face and a horizontal lower face cause downward bending of the light. As can be readily appreciated by one skilled in the art, in other embodiments, features 430 may be configured such that light may be directed in other directions.

FIG. 4B depicts a SLE 405 comprising an optical element 410 for focusing an incident optical beam, according to an embodiment. The SLE 405 is an embodiment of the SLE 100 described above in conjunction with FIG. 1. The SLE 405 comprises a construction 440 configured to focus an incident light beam generated by LPA 420. The construction 440 includes an optical element 410 and a plurality of features 430 emerging from a front body 415. The construction 440 is configured to focus a light beam to a point 460. In FIG. 4B, the features 430 associated with the construction 450 are configured in a saw tooth configuration, but the orientation of the tooth-like features 430 is exchanged in the lower half of the construction 440. The feature 430 at between the two sets of features 430 is configured as a plano-convex lens such that its focal point coincides with focal point 460. Such a construction 440 causes rays from the incident light beam striking the upper and lower halves of the beam to meet at focal point 460. Rays passing through the center converge at the focal point of the lens formed by feature 430. That is the construction 450 emulates the functionality of a convex lens. In other embodiments, the construction 450 may be configured to emulate the functionality of a concave lens with a focal point 450 located behind the construction 450.

FIG. 4C depicts a SLE 407 for shaping the incident optical beam, according to an embodiment. The SLE 407 is an embodiment of SLE 100 and includes an optical beam generated by the LPA 420 as well as an optical element 410, including a surface 470 emerging from the front body 415 for shaping the optical beam. A preset random function is used to define a surface 470 of the optical element. It should be noted that in various embodiments, the surface 470 may be realized by via one or more cells (e.g., cells 160) associated with the optical element 410. One or more reflective, diffractive, or any combination of reflective and diffractive properties associated with a cell 160 may generate the surface 470. For example, cells associated with the optical element 410 are configured to provide a combination of constructive and destructive interference based on the angle of an incoming optical beam. In other embodiments (not shown), one or more features (e.g., features 430) associated with the construction 440 may be utilized realize a surface 470 and shape the incident optical beam. A shaped incident optical beam may provide spatial filtering of the incident optical beam. For example, spatial filtering may be used to increase the directionality of the incident optical beam. In another embodiment, the surface 470 may be used to scatter an incident optical beam in order to illuminate a local area 330. As can be readily appreciated by one skilled in the art, in various other embodiments, the surface 470 may be used to provide other spatial filtering properties to an incident optical beam.

In one or more embodiments, the construction 440 comprising an optical element 140 and features 430 is configured to combine one or more of the optical functions performed by SLE 400, 401, and 402 described above in conjunction with FIGS. 4A-4C. For example, in one or more embodiments, a construction 440 comprising three optical elements 140 may focus, bend in a downward direction, shape a beam produced by an LPA 110. In various embodiments, optical functions such as focus, shape, etc. are performed by a construction 440 using one or more optical elements 140 to generate unique patterns in a local area. Moreover, in some embodiments, some or all of the components from some or all of FIGS. 4A-4C may be combined. For example, the SLE 400 may emit light that is coupled into the construction 440 that emits light that is coupled into an optical element 410 having a surface 470.

FIG. 5A shows a hand 510 being tracked by a light pattern comprising a plurality of horizontal bars 520 orientated parallel to the hand 510, in accordance with an embodiment. In FIG. 5A, it is apparent that the one or more horizontal bars associated with the generated light pattern comprising the horizontal bars 520 coincide with the axis of the fingers. Therefore, the determined information including data is limited and it is difficult to identify and track the shape of the object in the local area (e.g., hand 510 being tracked). However, the fingers may often be the points of major interest as fingers may provide gestures that the system uses as commands. For example, based on one or more gestures tracked, the system changes, automatically, the orientation of the bars (e.g., horizontal to vertical or vertical to horizontal). In other embodiments, the generated light pattern is a set of structured light generated by an optical element 140 associated with a SLE (e.g., the SLE 100). Examples of structured light include light patterns comprising horizontal or vertical bars, grids, or other geometrical objects configured to deform when striking a local area. Additional generated light patterns are described below.

Figure 5B:
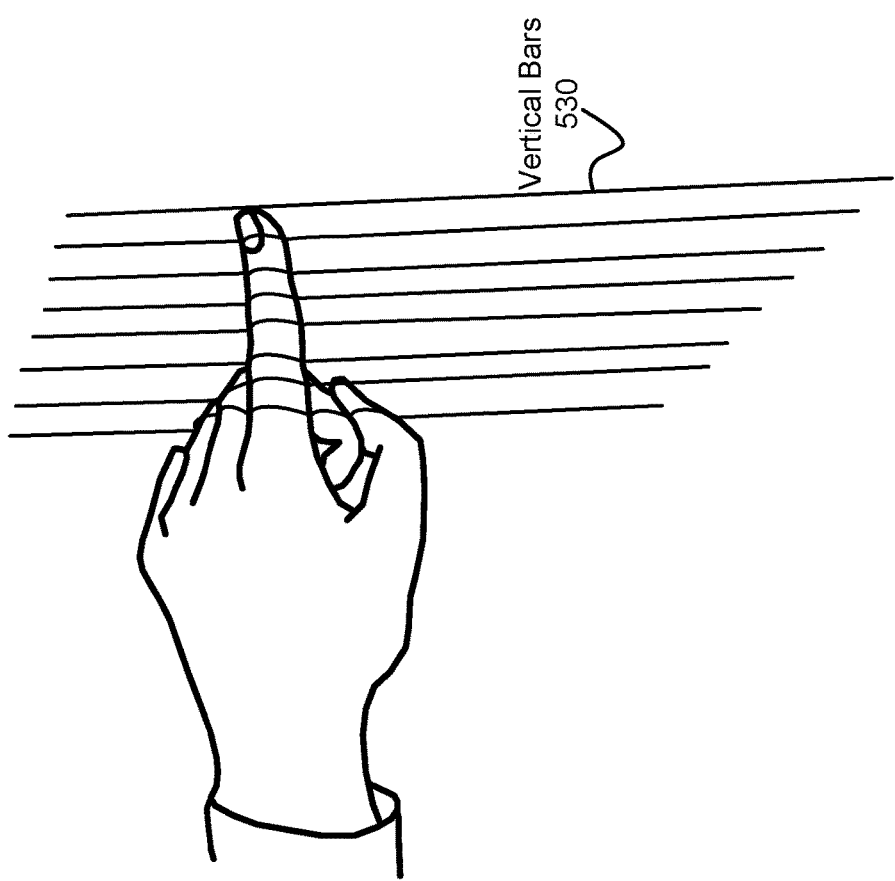
FIG. 5B shows a hand being tracked by a light pattern comprising a plurality of vertical bars, according to an embodiment.

FIG. 5B shows a hand 510 being tracked by a light pattern comprising a plurality of vertical bars 530, according to an embodiment. The vertical bars 530 are orientated perpendicular to the axis of the fingers associated with the hand 510. That is, the bars associated with the light pattern comprising vertical bars 530 lie across the fingers associated with the hand 510. Such a configuration of bars may provide more information regarding the object being tracked (e.g., the fingers associated with the hand 510). In one or more embodiments, the choice of structured light (e.g., vertical bars 520 or horizontal bars 530) is performed based on input to a processor associated with the SLE 100 described above in conjunction with FIG. 3. The process of selecting a structured element is further described below in conjunction with FIG. 8.

FIGS. 6A-E illustrate various changes that may be made to the light pattern generated by the SLE 100 in order to improve tracking, in accordance with one embodiment. FIGS. 6A-6E all contain two sets of bars wherein the first set represents a first light pattern and the second set of bars is the first light pattern after a change of one or more of parameters associated with the bars in the set. In FIGS. 6A-E described below, a changed parameter may be a spacing 620, a length 630, a density 640, a shape 650, and an intensity 660.

Figure 6A:
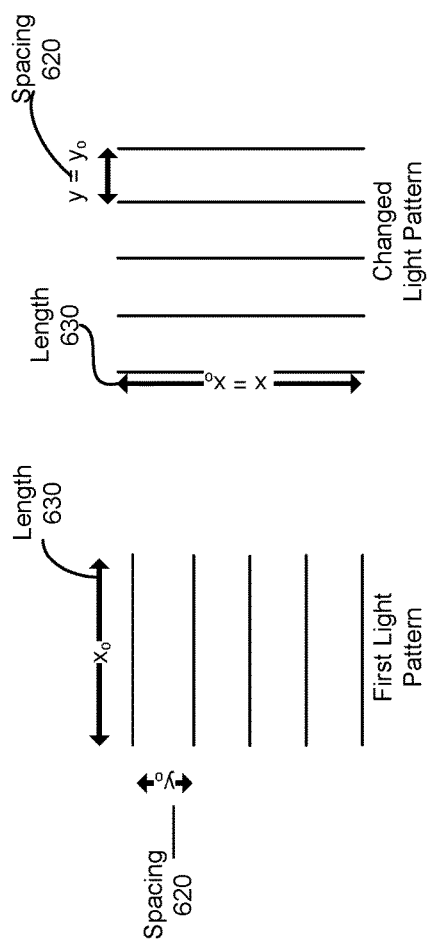
FIG. 6A shows a change in the orientation of the bars from horizontal to vertical, according to an embodiment, in accordance with an embodiment.

FIG. 6A shows a change in the orientation of the bars from horizontal to vertical, according to an embodiment. FIG. 6A depicts a first light pattern and a changed light pattern. The first light pattern includes a set of five bars with a spacing 620 of $y_o$ and a length 630 of $x_o$ while the changed light pattern comprises a set of five vertical bars with a spacing 620 of y and a length 630 of x. The spacing 620, $y_o$ and the length 630 $x_o$ are nominal spacing and lengths associated with an original configuration of bars. A change in orientation of the bars from horizontal or vertical maintains the maintains the length 630 and spacing 620 of the bars in the set. That is, as shown in FIG. 6A, the changed bars have a spacing 620 of $y=y_o$ and a length of $x=x_o$. In other embodiments, bars may undergo a change in orientation from vertical to horizontal while maintaining relationships between space 620 and length 630.

Figure 6C:
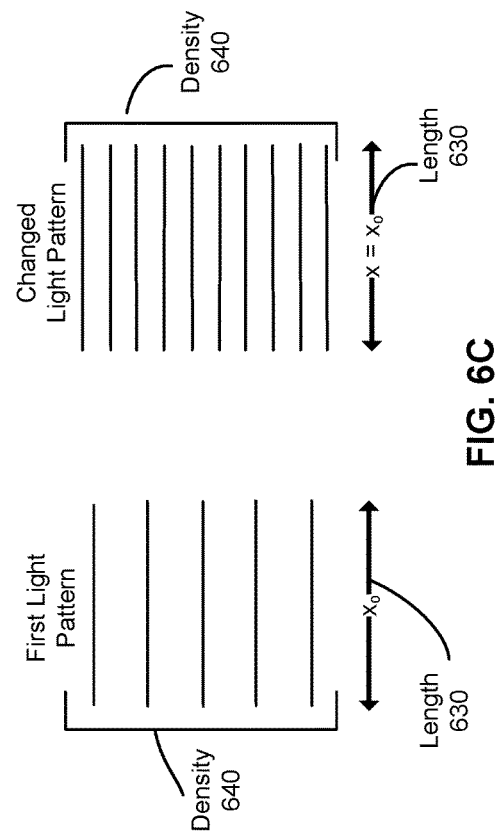
FIG. 6C shows an increase in density of the horizontal bars, in accordance with an embodiment.
Figure 6B:
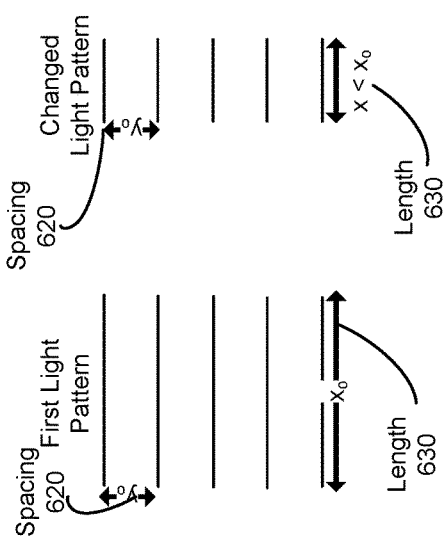
FIG. 6B shows a change in the orientation of the bars from horizontal to vertical, according to an embodiment, in accordance with an embodiment.

FIG. 6B shows a narrowing of the field of view resulting from a change in a set of bars, in accordance with an embodiment. FIG. 6B depicts a first light pattern and a changed light pattern. The first light pattern comprises a set of horizontal bars comprising a spacing 620 of $y_o$ and a length of $x_o$. As depicted in FIG. 6B, the changed light pattern comprises set of bars that maintain the spacing 620 between the bars but not the length 630. That is, in the changed light pattern the spacing 620 is $y_o$ and the length 630 is equal to a value x which is less than $x_o$. In various embodiments, such a decrease in length 630 may result in a corresponding narrowing of the field of view. It should be noted that, typically, a narrowing of the field of view may be useful with tracking objects. For example, in a case where fingers are a feature of interest and must be tracked a narrowing of the field of view is required. Alternatively, the field of view may be broadened by increasing the length 630 such that it is greater than the nominal length $x_o$. By way of example, a set of bars with a length 630 larger than $x_o$ are used to scan and locate a finger in a local area and once the fingers are found, the field of view is narrowed.

FIGS. 6C-E described in detail below, each, illustrate various light patterns that may be generated by the SLE 100 in order to track an object of interest in the depth dimension, in accordance with an embodiment.

FIG. 6C shows an increase in density of the horizontal bars, in accordance with an embodiment. The first light pattern comprises a set of five horizontal bars with a length 630, $x_o$, and a density 640, $u_o$. It should be noted that the parameter density 640 represents the number of bars in a given area. As shown in FIG. 6C the changed light pattern is the first light pattern of FIG. 6C with a ten horizontal bars. Said another way, the density 640 of the changed light pattern is larger than that of the first light pattern in FIG. 6D. Alternatively, if the number of horizontal bars in the changed light pattern of FIG. 6D was less than five, then the density 640 of the changed light pattern would be less than that of the first light pattern. In a still another example, a light pattern comprising a combination of high and low density bars is projected on local area 220 such that high density bars are projected on objects of interest. In other embodiments, bars may be vertical. High density 640 bars (horizontal or vertical bars) may be used to increase the resolution of an object being tracked in the depth dimension. In various embodiments, a particular orientation and density of a generated light pattern is dynamically controlled by controller 360.

FIG. 6D shows a change in shape of a projected pattern, in accordance with an embodiment. FIG. 6D comprises of a first light pattern comprising five solid horizontal bars 650 and a changed light pattern comprising five dashed horizontal bars 652. All other parameters such as spacing 620, length 630, and density 640 between the first light pattern and the changed light pattern are maintained. In various embodiments, patterns may be generated by an optical element 140. For example, an optical element may generate one or more triangles, squares, circles, ellipses, other irregular polygon, or some combination thereof. In one or more embodiments, the generated pattern is determined by the controller 360 and is further described below in conjunction with FIG. 8.

FIG. 6E shows changes in intensity of a projected pattern, in accordance with an embodiment. The first light pattern comprises two low intensity bars 660 as well as three high intensity bars. FIG. 6E delineates a changed light pattern in which the low intensity bars 660 of the first light pattern have been changed to high intensity bars 662 in and vice versa in the changed light pattern. The process of choosing a particular light pattern is further described below in conjunction with FIG. 8.

Figure 7:
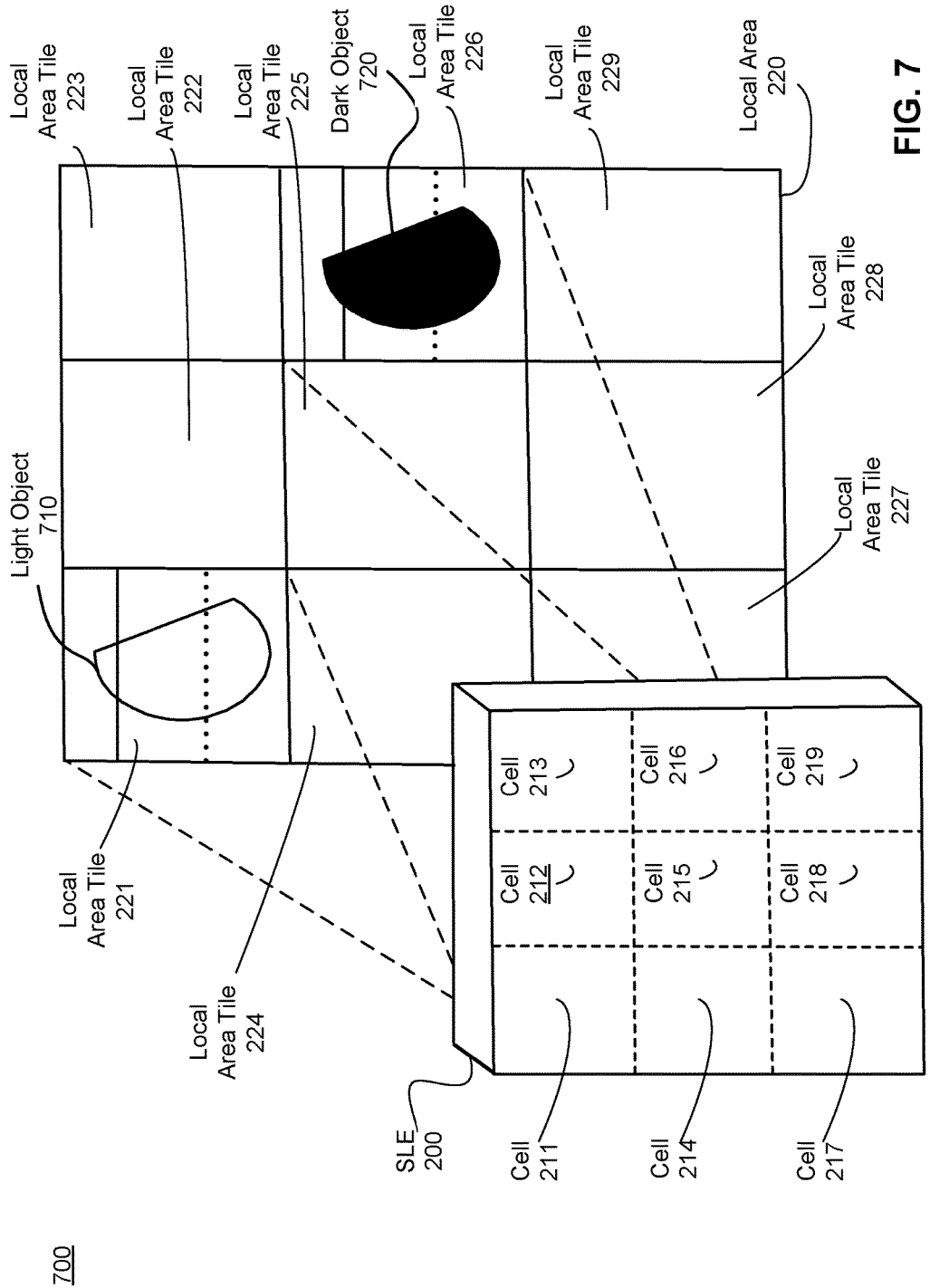
FIG. 7 illustrates a simplified schematic diagram of the SLE in FIG. 2A tracking a light object and a dark object, according to an embodiment.

FIG. 7 illustrates a simplified schematic diagram of the SLE 700 tracking a light object 710 and a dark object 720, according to an embodiment. SLE 700 depicted in FIG. 7 is an embodiment of SLE 200 depicted in FIGS. 2A-D. A light object 710 is an object with greater than a threshold amount of reflectance in one or more optical bands (e.g., IR, UV, visual). Similarly, a dark object 720, is an object with less than a threshold amount of reflectance in one or more optical bands. In various embodiments, the threshold amount of reflectance is predefined and stored in controller 360. In other embodiments, the threshold amount of reflectance is determined dynamically by the controller 360 based on one or more captured frames received from imager 350.

In FIG. 7, the light object 710 is located in the local area tile 221. Cell 211 may decrease the intensity of the bars 230, thereby increasing the resolution of the received tracking information as described above in conjunction with FIG. 6. In other embodiments, one or more cells 211-219 of a group of cells may illuminate local area tile 711. It should also be noted that in the illustration of the local area 220, a dark object 720, is found in local area tile 226. In various embodiments, local area tile 229 is illuminated by cell 219 and the intensity of the bars 230 is increased to increase the resolution of the tracking information received. In an embodiment, the cells 221-229 receive information regarding bar 230 intensity from a processor as described below in conjunction with FIG. 8. The different cells 211-219 are able to operate independently and each cell 211-219 may be individually controlled to react appropriately to the one or more objects in the associated local area tile 221-229.

FIG. 8 is a simplified flow diagram illustrating a method for modifying the pattern in one or more cells 160 in accordance with an embodiment. In one embodiment, the process of FIG. 8 is performed by the tracking system 300. In some embodiments, other devices may perform some or all of the steps of the process in other embodiments. Likewise, embodiments may include different and/or additional steps, or perform the steps in different orders.

The tracking system illuminates a 3D space with an initial laser configuration. Illuminating a local area may involve representing an initial laser configuration associated with a previously generated pattern. In one or more embodiments, an initial laser configuration the previous laser configuration that was previously used to capture a frame. In other embodiments, the tracking system provides instructions to a SLE to illuminate the local area with a previously used laser configuration.

The tracking system 300 captures 820 an image frame. For example, the frame may be captured using the imager 350. In various embodiments, frame may be captured in one or more electromagnetic bands (e.g., UV, IR, visible). The process of capturing a frame is further described above in conjunction with FIG. 3.

The tracking system 300 analyzes 830 the captured frame. In various embodiments, the frame is analyzed 830 via one or more standard two-dimensional signal processing techniques the output of which are a set of characteristics or parameters related to the frame. For example, the analysis information may extract depth information (i.e., distance from the imager) from the captured frame such that a depth is associated with each object in the frame.

In some embodiments, the tracking system performs a lookup of stored analysis guidelines associated with the captured frame. That is, for any particular configuration, there may be ones or more predefined analysis guidelines associated with an procedure for performing an analysis. An example analysis guideline may be, "determine a threshold level of luminosity; determine a special variance." In other embodiments, guidelines may involve instructions for one or more digital image processing techniques The tracking system 300 determines 840 a new laser configuration including one or more optical functions to apply. A new laser configuration may be associated with a change in modulation (i.e., diffractive, refractive or some combination of diffractive and refractive modulation), one or more optical function, a change in pattern, or some combination thereof. It should be noted that in one or more embodiments, the new laser configuration is the initial laser configuration. That is, in some situations based on the captured frames, the controller 360 may determine that no change to the current laser configuration is needed.

The tracking system 300 updates 850 the laser configuration with the new laser configuration and the process flow moves to 810, which illuminates the local area using the updated laser configuration.

Additional Configuration Information

The foregoing description of the embodiments of the disclosure has been presented for the purpose of illustration; it is not intended to be exhaustive or to limit the disclosure to the precise forms disclosed. Persons skilled in the relevant art can appreciate that many modifications and variations are possible in light of the above disclosure.

Some portions of this description describe the embodiments of the disclosure in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the disclosure may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the disclosure may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the disclosure, which is set forth in the following claims.

What is claimed is:

1. A system comprising:
an optical element that comprises a plurality of cells that are each aligned with a respective subset of an array of lasers, such that each cell receives light from a corresponding laser of the array of lasers, and each cell individually and dynamically applies a modulation to the received light passing through the cell to form a corresponding portion of a structured light pattern that is projected into a local area, wherein the structured light pattern includes at least a first portion and a second portion that has a different modulation than that of the first portion, the first portion and the second portion generated by the plurality of cells, and the first portion of the structured light pattern is projected into the local area.

2. The system of claim 1, wherein the modulation is one member of a group comprising: a diffractive modulation, a refractive modulation, and a combination of a diffractive modulation and a refractive modulation.

3. The system of claim 1, wherein a subset of the array of lasers, of the at least two subsets, and its respective cells are constructed from a single molded element.

4. The system of claim 1, wherein a width of a cell, of the plurality of cells, is 1 mm or less.

5. The system of claim 1, wherein one or more cells are individually controllable to change modulation.

6. The system of claim 5, wherein the one or more of cells associated with an optical element are controllable to dynamically provide changes to the structured light pattern based on receiving and analyzing at least one captured frame, the frame comprising a plurality of pixels in a two-dimensional layout.

7. The system of claim 6, wherein the dynamic control is configurable to apply the structured light pattern with increased resolution to a first part portion of the structured light pattern and to apply the structured light pattern with reduced resolution to a second portion of the local area.

8. The system of claim 6, wherein changes to the structured light pattern comprise a change in at least one cell of a plurality of cells associated with an optical element.

9. The system of claim 6, wherein changes to the structured light pattern comprise a change in at least one cell of a plurality of cells associated with an optical element.

10. The system of claim 9, wherein changes to the structured light pattern comprise a change in at least one cell of a plurality of cells.

11. The system of claim 5, wherein the plurality of cells is further controllable with respect to a position and a shape of the generated structured light pattern.

12. A system comprising:
an optical element that comprises a plurality of cells that are each aligned with a respective subset of an array of lasers, such that each cell receives light from a corresponding laser of the array of lasers, and each cell individually and dynamically applies a modulation to the received light passing through the cell to form a corresponding portion of a structured light pattern that is projected into a local area, wherein the structured light pattern includes at least a first portion and a second portion that has a different modulation than that of the first portion, the first portion and the second portion generated by the plurality of cells, and the first portion of the structured light pattern is projected into the local area; and a controller configured to determine depth information for one or more objects in the three-dimensional space using one or more images.

13. The apparatus of claim 12, wherein the modulation is one member of a group comprising: a diffractive modulation, a refractive modulation, and a combination of a diffractive modulation and a refractive modulation.

14. The system of claim 12, wherein a subset of the array of lasers, of the at least two subsets, and its respective cells are constructed from a single molded element.

15. The system of claim 12, wherein a width of a cell, of the plurality of cells, is 1 mm or less.

16. The system of claim 12, wherein one or more cells are individually controllable to change modulation.

17. The system of claim 16, wherein the one or more of cells are controllable to dynamically provide changes to the structured light pattern based on receiving and analyzing at least one captured frame, said frame comprising a plurality of pixels in a two-dimensional layout.

18. The system of claim 17, wherein the dynamic control is configurable to apply the structured light pattern with increased resolution to a first part portion of the structured light pattern and to apply the structured light pattern with reduced resolution to a second portion of the local area.

19. The system of claim 17, wherein changes to the structured light pattern comprise a change in at one cell of a plurality of cells.

20. The system of claim 16, wherein the plurality of cells are further controllable with respect to a position and a shape of the generated structured light pattern.

* * * * *

UNITED STATES PATENT AND TRADEMARK OFFICE
CERTIFICATE OF CORRECTION

PATENT NO. : 10,031,588 B2
APPLICATION NO. : 15/827816
DATED : July 24, 2018
INVENTOR(S) : Nitay Romano et al.

Page 1 of 1

It is certified that error appears in the above-identified patent and that said Letters Patent is hereby corrected as shown below:

In the Claims

Column 20, Line 12, after "at" insert -- least --.

Signed and Sealed this
Seventh Day of May, 2019

Andrei Iancu
*Director of the United States Patent and Trademark Office*